US010585023B2

(12) United States Patent
Broyer et al.

(10) Patent No.: US 10,585,023 B2
(45) Date of Patent: Mar. 10, 2020

(54) METHOD AND DEVICES FOR TREATING BIOLOGICAL SAMPLES

(71) Applicant: BIOMERIEUX, Marcy l'Etoile (FR)

(72) Inventors: Patrick Broyer, Saint Cassien (FR); Pradip Patel, Grezieu la Varrenne (FR); Nicole Pamme, Beverley (GB); Emilie Bisceglia, Lyons (FR)

(73) Assignee: BIOMERIEUX, Marcy l'Etoile (FR)

( * ) Notice: Subject to any disclaimer, the term of this patent is extended or adjusted under 35 U.S.C. 154(b) by 146 days.

(21) Appl. No.: 15/521,595

(22) PCT Filed: Oct. 23, 2015

(86) PCT No.: PCT/FR2015/052849
§ 371 (c)(1),
(2) Date: Apr. 24, 2017

(87) PCT Pub. No.: WO2016/062975
PCT Pub. Date: Apr. 28, 2016

(65) Prior Publication Data
US 2017/0241878 A1 Aug. 24, 2017

(30) Foreign Application Priority Data
Oct. 24, 2014 (FR) .................................. 14 60253

(51) Int. Cl.
| | | |
|---|---|---|
| G01N 1/40 | (2006.01) | |
| G01N 15/02 | (2006.01) | |
| B01L 3/00 | (2006.01) | |
| C12N 13/00 | (2006.01) | |
| C12Q 1/24 | (2006.01) | |
| G01N 27/447 | (2006.01) | |
| C12N 1/02 | (2006.01) | |
| G01N 1/44 | (2006.01) | |
| G01N 15/00 | (2006.01) | |

(52) U.S. Cl.
CPC ...... *G01N 1/4077* (2013.01); *B01L 3/502753* (2013.01); *B01L 3/502776* (2013.01); *C12N 1/02* (2013.01); *C12N 13/00* (2013.01); *C12Q 1/24* (2013.01); *G01N 1/40* (2013.01); *G01N 15/0255* (2013.01); *G01N 27/447* (2013.01); *G01N 27/44704* (2013.01); *B01L 3/502715* (2013.01); *B01L 2200/0652* (2013.01); *B01L 2300/0816* (2013.01); *B01L 2300/0829* (2013.01); *B01L 2300/0864* (2013.01); *B01L 2300/0867* (2013.01); *B01L 2300/0887* (2013.01); *B01L 2400/0436* (2013.01); *G01N 1/44* (2013.01); *G01N 2001/4094* (2013.01); *G01N 2015/0065* (2013.01)

(58) Field of Classification Search
CPC ........ C12N 13/00; C12N 1/02; G01N 1/4077; G01N 2001/4094; G01N 15/1459; G01N 2015/1006; G01N 2015/1081; G01N 2015/1409; G01N 2015/142; G01N 15/0255; G01N 15/1484; G01N 1/40; G01N 1/44; G01N 2001/4088; G01N 2015/0065; G01N 2015/0088; G01N 2015/149; G01N 27/447; G01N 27/44704; G01N 33/12; G01N 15/10; G01N 29/222; G01N 2015/0053; G01N 33/5005; G01N 33/54313; G01N 33/574; B01L 2200/0652; B01L 2300/0816; B01L 2300/0887; B01L 2400/0436; B01L 3/502753; B01L 2300/0829; B01L 2300/0864; B01L 2300/0867; B01L 3/5027; B01L 3/502715; B01L 3/502776; B01L 3/502761; A61J 1/10; A61J 1/2003; A61J 1/2089; A61J 3/00; A61K 35/12; A61K 9/0019; A61M 1/3678; A61M 1/3692; A61M 1/3693; A61M 2205/10; A61M 37/00; A61M 5/1407; A61M 5/1413; A61M 5/19; B65B 3/003; C12Q 1/24; B03B 7/00
See application file for complete search history.

(56) References Cited

U.S. PATENT DOCUMENTS

2004/0069717 A1    4/2004    Laurell et al.

FOREIGN PATENT DOCUMENTS

| WO | 02/072234 A1 | 9/2002 |
| WO | 2008/122051 A1 | 10/2008 |
| WO | 2014/046605 A1 | 3/2014 |

OTHER PUBLICATIONS

Thomas Laurell et al. "Chip Integrated Strategies for Acoustic Separation and Manipulation of Cells and Particles", Chemical Society Reviews, Chemical Society, London. GB, vol. 36, No. 3, Mar. 1, 2007, pp. 492-506.
Per Augustsson et al., "Decomplexing Biofluids Using Mircochip Based Acoustophoresis", Lab on a Chip, vol. 9, No. 6, Jan. 1, 2009, pp. 810-818.
Lukas Krasny et al., "Identification of Bacteria Using Mass Spectrometry Techniques", International Journal of Mass Spectrometry, vol. 353, Nov. 1, 2013, pp. 67-79.
Alex Van Belkum et al., "Next-Generation Antimicrobial Susceptibility Testing", Journal of Clinical Microbiology, vol. 51, No. 7, Jul. 1, 2013, pp. 2018-2024.
Janne Lehtinen et al., "Real-Time Monitoring of Antimicrobial Activity with the Multiparameter Microplate Assay", Journal of Microbiological Methods, Elsevier, Amsterdam, NL, vol. 66, No. 3, Sep. 1, 2006, pp. 381-389.
Nov. 1, 2016 Search Report issued in International Patent Application No. PCT/FR2015/052849.
Jan. 11, 2016 Written Opinion issued in International Patent Application No. PCT/FR2015/052849.
Ai Y. et al., "Seperation of *Escherichia coli* Bacteria from Peripheral Blood Mononuclear Cells Using Standing Surface Acoustic Waves" Analytical Chemistry, (2013), vol. 85, pp. 9126-9134.

*Primary Examiner* — Deborah K Ware
(74) *Attorney, Agent, or Firm* — Oliff PLC

(57) ABSTRACT

A method of treating a biological sample, preferably a sample of blood or bodily fluids likely to contain one or more species of interest, and including a step of decomplexification by acoustophoresis (as well as associated systems, devices, substrates and connection devices).

23 Claims, 18 Drawing Sheets

Section A-A

Section B-B

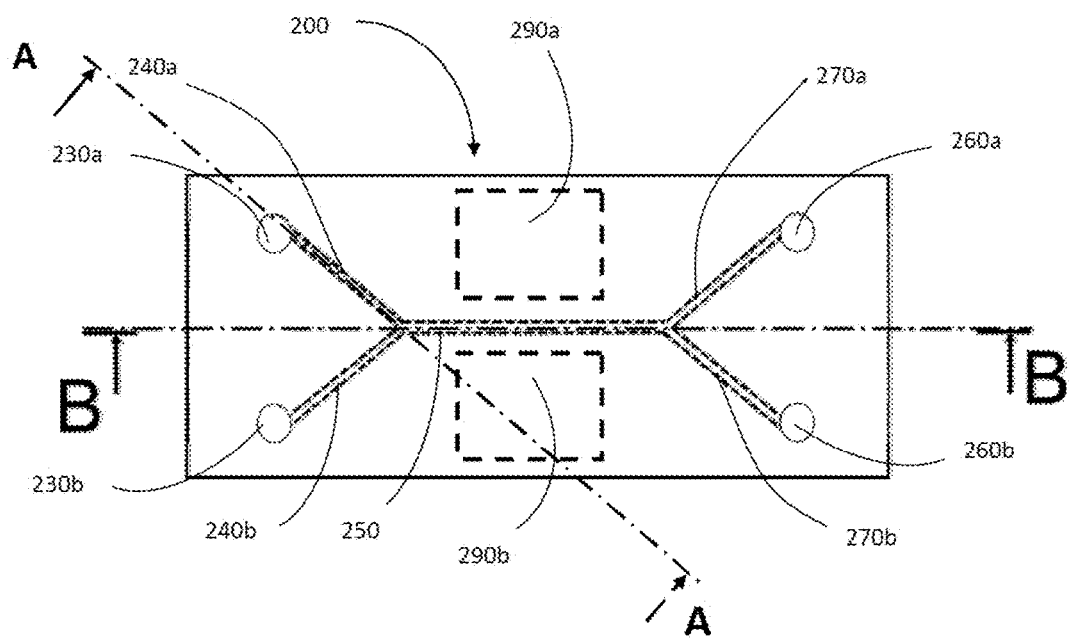
Figure 4
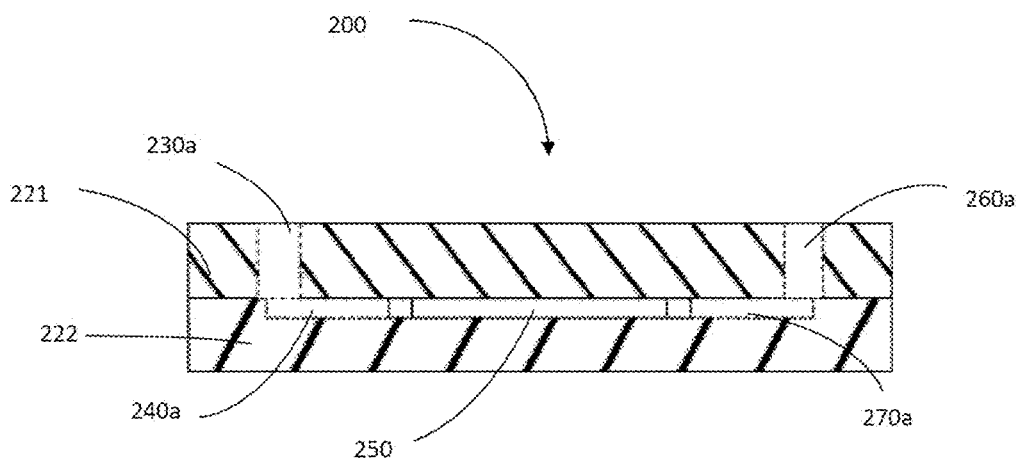
Figure 5a – Section B-B

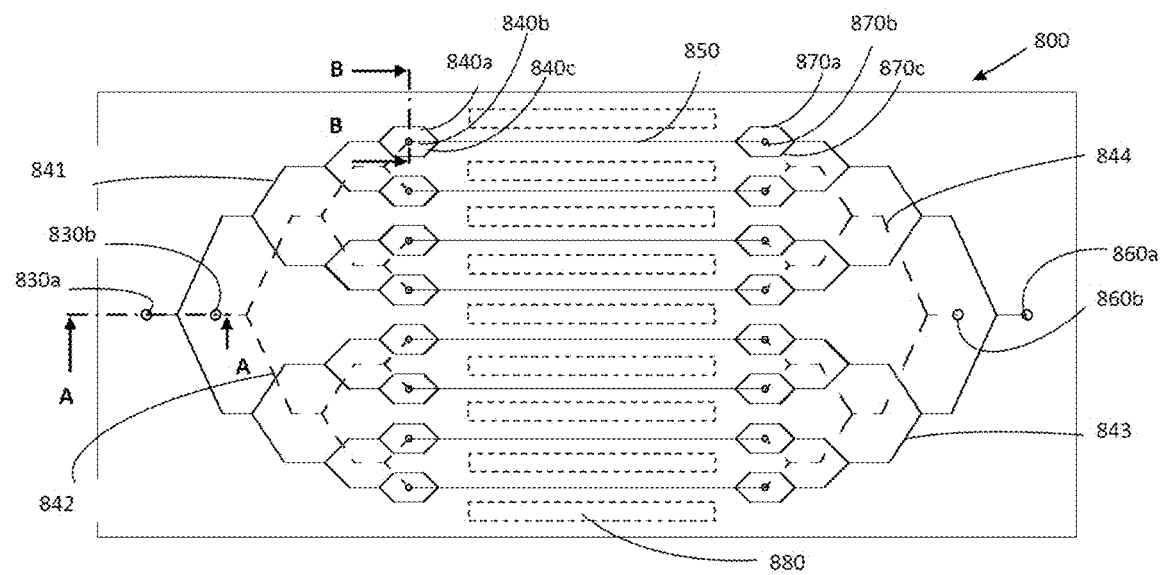
Figure 11
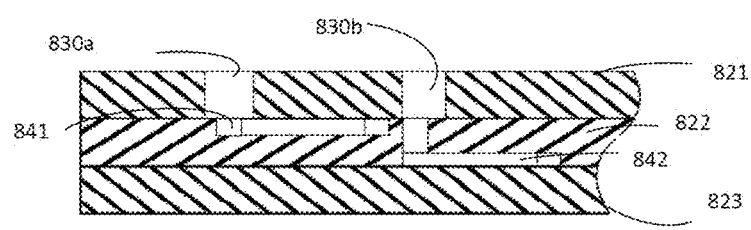
Figure 12a - Section A-A
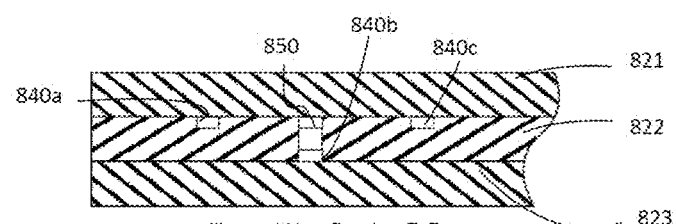
Figure 12b - Section B-B

METHOD AND DEVICES FOR TREATING BIOLOGICAL SAMPLES

The method and the devices according to the invention are of interest in the treatment of biological samples, in particular in the field of tests on biological samples from whole blood, from blood cultures or from body fluids.

Processes for preparing complex biological or chemical samples call for operations to separate the particles, cells or molecules in order to make possible or facilitate the analysis of particles, cells or molecules of interest, which may be contained in the sample. An objective of these sample preparation processes is thus to separate and/or concentrate the particles, cells or molecules of interest with respect to non-specific elements in order to enable, for example, their capture and/or detection.

Among the conventional processes for separating particles, centrifugation, filtration, chromatography or electrophoresis are very widely used for the preparation of complex biological or chemical samples. However, these methods are often painstaking to implement and do not make it possible to treat large volumes of samples. For example, filtration processes make it necessary to treat a defined volume of sample and then to perform a filter cleaning operation in order to prevent any blockage. This technique does not therefore make it possible to treat a complex biological or chemical sample in continuous flow. Furthermore, conventional techniques for preparing a biological sample, in particular chemical lysis or selective lysis, do not make it possible to ensure or can limit the viability of live cells such as bacteria following the preparation of the sample, and can thus have an impact on the quality of the subsequent capture, regrowth and/or detection steps.

Conventional processes for preparing blood samples of large volumes, greater than 10 ml, and which may contain microorganisms, mostly use chemical lysis followed by centrifugation. These processes use in particular detergents such as a selective lysis buffer for human cells. The use of detergents is however known to have an impact on bacterial stress and leads to an extension of the time for returning to the exponential phase of the bacteria extracted with these processes. This step is important and necessary in order to carry out detection of the microorganisms but can also kill the microorganisms present in a low concentration or make their return to growth less rapid.

Conventional processes for extracting blood samples by centrifugation, gel tube or filtration also requires several steps generally carried out manually and requiring significant equipment associated with the use of several steps for removing supernatant and with the addition of various washing buffers.

Processes for separating particles, cells or molecules in continuous flow using microfluidic devices can make it possible to treat large sample volumes, this being by continually introducing the sample into the microfluidic device. The principle of acoustophoresis in a microfluidic device has, for example, already been applied for the separation of *Escherichia coli* bacteria in a sample containing peripheral blood mononuclear cells [1]. However, this process can only be used on a highly diluted blood sample, thereby making it inapplicable to a continuous-flow blood sample analysis.

With regard to the problems presented above, an objective of the present invention aims to develop a device and the process(es) associated therewith making it possible:

to provide a simplified and universal process which makes it possible to treat and analyze blood samples of various types, in particular samples of whole blood, samples originating from blood cultures, samples of sterile body fluids enriched in culture medium or of non-sterile body fluids;

to provide a process for treating a sample from a blood culture or a sample of sterile body fluid not using a selective lysis buffer and/or not using prior dilution of the sample before it is introduced into the acoustophoresis device and allowing the extraction of the microorganism(s) contained in the sample;

to provide a method of treatment guaranteeing the viability of the microorganisms;

to provide a process which allows a faster return to growth phase of the pathogenic agents present in the biological sample;

to decomplexify and/or to concentrate particles, cells or molecules of interest at high flow rates, in particular flow rates greater than 1 µl/min per separation channel;

to limit the production of non-specific elements which may distort the final result of the analysis;

to provide a method for treating a biological sample which facilitates the obtaining of an identification of the microbiological species and/or of an antibiogram profile;

to limit as much as possible the risks of contamination of the sample and/or of the environment and/or of the laboratory technician;

to simplify the biological sample treatment protocol, in order to reduce the operating time, the number of materials and consumables used and the risk of errors and to improve reproducibility;

to provide devices and a method compatible with all of the known methods of analysis (microbiology, culture, virology, bacteriology, immunoassays, metasequencing, PCR, etc.);

to provide several associated microfluidic devices, supports and systems capable of carrying out methods for treating biological samples by acoustophoresis, in particular methods according to the invention.

The present invention relates to a method and various associated devices allowing the decomplexification of biological samples, in particular of blood samples, of samples from blood cultures, or else of samples of body fluids, thus allowing the analysis of microorganisms which are contained or which may be contained in the biological sample.

In order to achieve this objective and to overcome the drawbacks of the abovementioned methods, the invention relates to a method for treating a biological sample which may contain one or more biological species of interest, comprising a decomplexification step, said decomplexification step comprising the following steps optionally, carrying out a step of enrichment of the biological sample, preferentially by incubation in the presence of a culture medium, introducing all or part of this sample into a first inlet orifice of an acoustophoresis device, introducing a buffer into a second inlet orifice of the acoustophoresis device, the buffer preferentially being of different nature and/or of different density relative to the biological sample, said inlet orifices being fluidically connected to at least two outlet orifices by at least one separation channel, the buffer and the sample being introduced at respective flow rates capable of generating a laminar flow in the separation channel, carrying out a step of separation of said biological sample by acoustophoresis so as to promote the concentration of the non-specific particles present in the sample in at least one of the outlet orifices of said acoustophoresis device, optionally and following this decomplexification step, carrying out a step of determination of the presence, advantageously of identification, of one or more biological species in the sample, optionally and following this decomplexification step and a step of identification of the one or more biological species, carrying out a step of determination of the antibiogram profile of the biological species that has (have) been identified.

The term "non-specific particles" is intended to mean particles which can impair or limit the capture and/or the detection of one or more biological species of interest. Such particles may be, by way of example, formed elements of the blood or blood cells such as red blood cells, white blood cells, platelets, eukaryotic cells, aggregates of lipids or erythrocytes, etc.

Following this method, at least one of the outlet orifices of the device exhibits an enriched and decomplexified sample, that is to say its concentration of non-specific particles is reduced. This decomplexification step is thus analogous to a purification step in so far as it facilitates the detection and the subsequent analysis of the biological species of interest that is (are) present in the sample.

Following this method, at least one of the outlet orifices of the device, other than that comprising the enriched and decomplexified sample, exhibits a concentrated sample, that is to say its concentration of non-specific particles is increased.

Indeed, the majority of the non-specific particles are separated by the acoustophoresis separation step, since the non-specific particles such as the formed elements of the blood have a higher volume and/or density and/or a lower compressibility than the one or more biological species of interest, said particles are therefore more subject to the acoustic radiation pressure and are concentrated in one of the outlet orifices. Conversely, the specifies of interest is (are) less subject to the effect of the acoustic wave by virtue of its (their) size, its (their) density and its (their) compressibility. Said species will thus be distributed predominantly by the circulation of the fluid containing them at the time they are introduced into the device. Depending on the geometry of the device and the orientation of the acoustic wave in the separation channel, the non-specific particles can in particular be separated in the direction of an outlet orifice of which the conveying channel has an axis similar to and in the extension of that of the separation channel. This separation toward a "central" outlet orifice, the channel of which has an axis similar to that of the separation channel, can be carried out by applying an acoustic wave having a pressure node substantially centered about the longitudinal axis of the separation channel. The distribution of the one or more species of interest can, depending on its (their) volume, its (their) density and its (their) compressibility, be equitable between the outlet orifices or concentrated in at least one outlet orifice, other than that where the non-specific particles are concentrated.

The step of enrichment by incubation in the presence of a culture medium can use specific or non-specific culture media. By way of example of culture media, mention may be made of BHI (brain heart infusion broth). Culture media in a bottle, such as Bact/ALERT® Standard Aerobic (bioMérieux, ref 256789, France), BacT/ALERT® Standard Anaerobic (bioMérieux, ref 259790, France), BacT/ALERT® FA FAN® Aerobic (bioMérieux, ref 259791, France), BacT/ALERT® FN FAN® Anaerobic (bioMérieux, ref 259793, France) or BacT/ALERT® PF Pediatric FAN® (bioMérieux, ref 259794, France), can also be used.

In the case of the treatment of non-sterile body fluids, such as bronchoalveolar lavages, the incubation step is not necessary. This is because the concentration of microorganisms of these samples is approximately between $10^4$ CFU per ml and $10^5$ CFU per ml with $10^6$ eukaryotic cells per milliliter. The advantage is to remove, by means of the treatment method according to the invention, any human DNA which is present in a ratio of 20000:1 relative to the microbial DNA. The preparation method thus makes it possible to carry out a microbial DNA analysis step following the decomplexification step, in particular a sequencing or amplification step of PCR (Polymerase Chain Reaction) or qPCR (quantitative Polymerase Chain Reaction) type. For these samples, the decomplexification step thus makes it possible to separate the natural flora from the eukaryotic cells, so as to analyze only the microbial DNA during the analysis step. In order to prepare the decomplexified sample for this microbial DNA analysis step, said sample undergoes a step of mechanical or enzymatic lysis followed by a nucleic acid purification step.

The advantage is thus a time saving with respect to conventional protocols of differential lysis and of digestion of the nucleic acids and easier automation making it possible to dispense with the need for qualified labor. The decomplexification step by acoustophoresis optionally makes it possible to extract the viruses, whereas a conventional method of selective lysis does not make it possible to recover envelope viruses, the latter being lyzed like the eukaryotic cells.

In the case of the treatment of a whole blood sample, the step of incubation in culture medium can be reduced by 2 to 4 at a temperature of between 35° C. and 37° C., in order to obtain an amount of one or more biological species of interest of approximately between $10e^2$ and $10e^4$ CFU/ml, this amount being sufficient to determine the presence of a biological species in the sample. Furthermore, this step allows the biological species of interest that is (are) present in the biological sample to reach an exponential growth phase. This growth stage makes it possible in particular to improve the yield of an antibiotic sensitivity test carried out on the one or more biological species of interest, the slowing down or inhibition of its (their) growth by the antibiotic being easier to observe.

"CFU" means "Colony Forming Unit".

Performing a step of determination of the presence of a biological species in the sample can in particular be carried out using systems sold by the applicant, such as BacT/ALERT® VIRTUO™ (bioMérieux, France). This system makes it possible to detect the presence of one or more biological species of interest such as microorganisms in blood samples when said presence reaches a concentration between $10e^7$ and $10e^9$ CFU/ml. For this, a volume of sample is dispensed into a culture bottle containing a liquid culture medium and then placed in an incubator. Various types of bottles make it possible to promote the growth of particular microorganisms. The bottle is monitored during the incubation, which can last up to 72 h, and a positive growth signal is given if the concentration reaches a predetermined threshold.

Buffer solutions which can be used are, for example, and in a non-limiting manner:

Neutral buffers, for example water, a 0.85% NaCl solution, phosphate buffered saline (PBS), etc.

Non-specific (generic) buffers for return of microorganisms to growth. By way of example, these buffers may be of BHI (brain heart infusion broth), TSB (trypticase soy broth) or BPW (buffered peptone water) type. These buffers make it possible in particular to place the microorganisms directly in a medium conducive to return to growth before a cytometry analysis step.

Microorganism-specific buffers for return to growth. By way of example, these buffers may be of the type: Fraser 1/2, LX broth (*Listeria* Xpress broth; Ref. 42626 bioMérieux, France), LMX broth (*Listeria Monocytogenes* Xpress broth; bioMérieux, France) or SX broth (*Salmonella* Xpress broth; Ref. 42118 bioMérieux, France).

Buffers with a density that is either lower or higher than the density of the biological sample; the density of the sample is supposed to be close to 1. By way of example, these buffers can comprise: (silanized) colloidal silica, Iohexol (Nycodenz®), Iodixanol (OptiPrep™), Ficoll 400, Dextran 70, Dextran 200, Dextran 500, sucrose, cesium chloride, perfluorocarbon fluids, mineral oils, silicone oils, oils for immersion microscope lenses, Pluronic® F127, polyethylene oxide, polyvinyl alcohol, hydroxypropylmethylcellulose, xanthan gum.

Another example of a buffer that can be used is a biocompatible isotonic buffer such as physiological saline adjusted with a volume ratio of 10% v/v, 5% v/v, preferentially 1% v/v of Percoll® (Sigma Aldrich). Percoll® comprises particles of silica with a diameter of from 15 to 30 nm, coated with polyvinylpyrrolidone (PVP).

Advantageously and in so far as the device used with the method according to the invention comprises at least three inlet orifices and three conveying channels of these orifices to the separation channel, two different buffer solutions are introduced into two different inlet orifices. The use of two different buffer solutions makes it possible to facilitate the passage of certain particles or microorganisms from one liquid introduced to another during the step of separation by acoustophoresis, by adjusting in particular the differences in density between the buffer solutions introduced.

More particularly, the biological sample is introduced into an acoustophoresis device so as to be conveyed by at least two conveying channels to the separation channel, the device being arranged to obtain a laminar flow in the separation channel between the flows of sample and of buffer solution originating from the conveying channels.

Advantageously, the treatment method according to the invention comprises a second decomplexification step comprising carrying out a second step of separation of said concentrated sample by acoustophoresis so as to promote a greater recovery rate of the species of interest that is (are) still present in the concentrated sample in at least one of the outlet orifices of said acoustophoresis device.

The recovery rate of the biological species is defined as the ratio of the number of biological species in the outlet orifice in question to the total number of biological species in all the outlet orifices of the device.

This second step of decomplexification of said biological sample by acoustophoresis is carried out on the part of the sample resulting from the first separation and containing predominantly non-specific particles. This second separation makes it possible to increase the recovery rate, or collection yield, of the microorganisms present in the biological sample by promoting a second time the concentration of the non-specific particles, such as formed elements of the blood, present in the concentrated sample, in one of the orifices of said acoustophoresis device. This is because the microorganisms entrained with the non-specific particles during the first separation are capable of being separated by acoustophoresis and thus being able to be collected following this second separation.

This second step of decomplexification by acoustophoresis can be carried out by reintroducing the concentrated sample into a single acoustophoresis device comprising at least two successive separation channels.

Alternatively, this second separation step can be carried out by means of the following steps:
  introducing all or part of the sample concentrated subsequent to the first separation step into an inlet orifice of an acoustophoresis device, this device being identical to or different than the first device used during the first separation step,
  introducing a buffer into a second inlet orifice of said acoustophoresis device, the buffer preferentially being of different nature and/or of different density relative to the biological sample,
  said inlet orifices being fluidically connected to at least two outlet orifices by a separation channel,
  the buffer and the sample being introduced at respective flow rates capable of generating a laminar flow in the separation channel,
  carrying out a second step of separation of said decomplexified sample by acoustophoresis so as to promote a greater recovery rate of the biological species still present in the concentrated sample in at least one of the outlet orifices of said acoustophoresis device.

Advantageously, the treatment method according to the invention comprises a second decomplexification step comprising carrying out a second step of separation of said decomplexified sample by acoustophoresis so as to promote a greater rejection rate of the non-specific elements, such as formed elements of the blood, present in the decomplexified sample in at least one of the outlet orifices of said acoustophoresis device. This is because a residual amount of non-specific particles is capable of being entrained in the decomplexified sample with the microorganisms during the first separation and can thus be separated and concentrated following this second decomplexification step.

The rejection rate of the non-specific elements is defined as the ratio of the number of non-specific elements in the outlet orifice in question to the total number of non-specific elements in all the outlet orifices of the device.

This second step of decomplexification by acoustophoresis can be carried out by reintroducing the decomplexified sample into a single acoustophoresis device comprising at least two successive separation channels.

Alternatively, this second separation step can be carried out by means of the following steps:
  introducing all or part of the sample decomplexified subsequent to the first separation step into an inlet orifice of an acoustophoresis device, this device being identical to or different than the first device used during the first separation step,
  introducing a buffer into a second inlet orifice of said acoustophoresis device, the buffer being preferentially of different nature and/or of different density relative to the biological sample,
  said inlet orifices being fluidically connected to at least two outlet orifices by a separation channel,
  the buffer and the sample being introduced at respective flow rates capable of generating a laminar flow in the separation channel, carrying out a second step of separation of said decomplexified sample by acoustophoresis so as to promote a greater rejection rate of the non-specific particles such as formed elements of the blood present in the decomplexified sample in at least one of the outlet orifices of said acoustophoresis device.

Advantageously, the treatment method according to the invention comprises an additional step of identification of the biological species following the obtaining of an enriched and decomplexified sample. This step is preferentially carried out by centrifugation and concentration in one step of all or part of the concentrated sample pellet followed by an analysis by mass spectrometry. A known rapid technique for rapid identification is analysis using a MALDI-TOF spectrometer of a fraction of the microorganism concentrate obtained after centrifugation and concentration. This fraction is for example of 1 µl. A piece of equipment that can be used for carrying out this step is the VITEK® MS sold by the applicant. The advantage of combining this type of identification with a step of separation by acoustophoresis is that of being able to have a decomplexified sample which can be used for the mass spectrometry analysis. The decomplexified sample can, for this, be centrifuged and then resuspended in a suitable buffer such as pure water. The centrifugation step can alternatively be carried out directly in the presence of deionized water, ethanol and/or formic acid, HCCA matrix and acetonitrile in order to directly extract the proteins from the microorganisms to be deposited on the MALDI-TOF MS analysis plate. Alternatively, it is possible to perform a second acoustophoresis step with a suitable buffer such as pure water, compatible with the spectrometry analysis step; the microorganisms present in the decomplexified sample are mixed with the buffer by acoustophoresis and are then in the concentrated sample. This concentrated sample can be directly used for a mass spectrometry analysis.

This identification step can also be carried out by plating out on a culture medium. Specific or non-specific culture media can be used for this identification step. Preferentially, selective media such as chromogenic media can be used. The advantage of combining this type of identification with a step of separation by acoustophoresis is that of being able to have a decomplexified sample that can be directly used to inoculate the culture medium. The inoculation of the culture medium can be carried out without any intermediate step, by taking the decomplexified sample from an outlet orifice of the device.

Advantageously, the treatment method according to the invention comprises carrying out an antibiogram test of the one or more biological species of interest following the obtaining of an enriched and decomplexified sample, preferentially carried out by flow cytometry, by means of a biochemical test or by early imaging of the inhibitory zones obtained on culture medium using an antibiotic disk or Etest® antibiotic strips (bioMérieux, France). This step may be subsequent to an identification step or may be begun in parallel with the identification step. For example, in so far as the antibiogram test comprises a first step of incubation of the sample, said step can be started before knowing the result of the identification step.

The performing of an antibiogram test by flow cytometry can be carried out by several methods. A first way consists in placing the one or more biological species of interest in the presence of one or more antibiotic(s) at different concentrations. The antibiotic(s) of interest are advantageously determined by the result of the identification step previously defined. Following a fluorescent labeling step, which will subsequently be defined, the samples obtained are successively suctioned in a cytometer in order to obtain an antibiogram profile as a function of the mean fluorescence of the microorganisms analyzed for each of the concentrations of antibiotic.

This test thus makes it possible to reliably and rapidly characterize a response of the one or more species of interest to the presence of the antibiotic, such a response being commonly classified according to one of the following three statements: susceptible, intermediate or resistant. The term "susceptible" is intended to mean that growth, or even survival, of the one or more species of interest in the presence of the antibiotic is impossible starting from a certain concentration of antibiotic. The term "intermediate" is intended to mean that growth of the one or more species of interest in the presence of the antibiotic is compromised, starting from a certain concentration. The term "resistant" is intended to mean that growth of the species one or more of interest in the presence of the antibiotic is possible.

An antibiotic within the meaning of the present invention can be replaced with an antifungal, an antimycobacterial or an analogous compound.

The performing of an antibiogram test by flow cytometry can also be carried out according to a second method. For this, a first count of the species of interest that is (are) present in a part of the decomplexified and enriched sample is carried out by flow cytometry. A second part of the decomplexified and enriched sample is placed in the presence of one or more antibiotic(s) at different concentrations for a given time, for example for 1 h to 35 h. The antibiotic(s) of interest are advantageously determined by the result of the previously defined identification step. Following this period of time, a second count of the species of interest that is (are) present in the second part of the sample in the presence of the antibiotic(s) is carried out by flow cytometry. Depending on the result of the count and on the antibiotic concentrations, an antibiogram profile is produced. This method makes it possible to dispense with a fluorescent labeling step.

The performing of an antibiogram test of the one or more biological species of interest can also be carried out by, immediately after the extraction by acoustophoresis, flooding the decomplexified sample onto agar culture medium (manually or by means of an automated device) and by incubating these culture media in order to initiate growth of the microorganisms. Once the identification is known, preferentially by means of the mass spectrometry technique, the appropriate antibiotic disks or Etest® antibiotic strips (bioMérieux, France) are selected and deposited on the dish(es) inoculated with the extract provided by the acoustophoresis device. The agar medium (media) is (are) incubated for 1 to 5 h while being monitored by means of a suitable imaging system which allows early measurement of the inhibitory zones and thus rapid provision of the antibiogram profile result by classification in three categories: Susceptible (S), Intermediate (I) or Resistant (R).

The performing of an antibiogram test of the one or more biological species of interest can also be carried out by means of biochemical tests. Systems sold by the applicant, such as the VITEK® 2 apparatus, thus make it possible to carry out an antibiogram in liquid medium in an automated manner. For this, all or part of the enriched and decomplexified sample is introduced into a VITEK® card for analytical purposes.

Advantageously, the treatment method according to the invention comprises a step of measurement of the optical density of the enriched and decomplexified sample during or following a step of separation by acoustophoresis so as to obtain a sample with a defined optical density, preferentially of between 0.025 and 0.5 McFarland. The optical density measurement can be carried out in the outlet orifice or in a collection tube. This step can in particular be carried out by diluting the enriched and decomplexified sample using a buffer solution, until a defined optical density is obtained. A sample with an optical density of between 0.025 and 0.5 McFarland can in particular be used for a subsequent incubation step allowing the microorganisms present in the sample to reach an exponential growth phase.

Advantageously, the treatment method according to the invention comprises a step of incubation of the decomplexified and enriched sample, preferentially between 30° C. and 37° C., preferentially for a period of 1 to 5 h, more preferentially of 2 h, the incubation possibly being carried out directly in the outlet orifice or the outlet collection tube. This step can allow the biological species of interest that is (are) present in the biological sample to reach an exponential growth phase. This growth stage makes it possible in particular to improve the yield of an antibiotic sensitivity test carried out on the one or more biological species of interest, the slowing down or inhibition of its (their) growth by the antibiotic being easier to observe.

Preferentially, this incubation step is carried out by shaking the decomplexified sample during the incubation. This shaking makes it possible for example to promote oxygenation of the sample, thus increasing the growth rate of aerobic microorganisms.

Preferentially and following the incubation step, the treatment method according to the invention comprises a step of measurement of the optical density of the enriched and decomplexified sample during or following the incubation step, preferentially after 2 h of incubation, so as to stop or prolong the incubation step or to adjust the dilution of the sample when a defined optical density threshold is measured. Said threshold is preferentially between 0.025 and 0.63 McFarland, more preferentially between 0.025 and 0.5 McFarland, alternatively between 0.5 and 0.63 McFarland. The optical density measurement can be carried out in the outlet orifice or in a collection tube. This step can in particular be carried out by diluting the enriched and decomplexified sample using a buffer solution, until a defined optical density is obtained. An optical density of between 0.025 and 0.63 McFarland can in particular make it possible to carry out a step of determination of sensitivity to an antibiotic by flow cytometry analysis. The sample is then sufficiently concentrated and the species of interest is (are) in the exponential growth phase.

Advantageously, the treatment method according to the invention comprises a step of analysis of the susceptibility of the sample to one or more antibiotic(s), preferentially carried out by flow cytometry or by means of a biochemical test, the antibiotic(s) being advantageously determined by the result of the step of identification of the one or more species of microorganism(s) that is (are) present in the concentrated sample. Since the choice of antibiotics that must be tested is restricted by the result of the identification step, the step of analysis of susceptibility of the sample to one or more antibiotic(s) can be carried out more rapidly and with a minimal number of manipulations.

Advantageously, following the decomplexification step, all or part of the enriched and decomplexified sample is transferred into the wells of a microplate or into various wells in fluidic connection with at least one of the outlet orifices containing all or part of the sample, preferentially from 3 to 7 wells, each of the wells possibly containing a different antibiotic and/or an antibiotic in different concentrations. Advantageously, the performing of a step of incubation of the enriched and decomplexified sample as previously defined is carried out directly in the wells of the microplate containing all or part of the sample. This incubation step can in particular last approximately 1 h at 35° C., without shaking, so as to leave the one or more species of interest sufficiently in the presence of the antibiotic(s) and to thus be capable of analyzing the continuation, the slowing down or the arrest of their growth, as a function of the various antibiotic concentrations.

Advantageously, the performing of a step of adjustment of the optical density of the enriched and decomplexified sample as previously defined is carried out directly in the wells of the microplate containing all or part of the sample.

Advantageously, each of the wells is, after an incubation time greater than or equal to 1 h in the presence of the antibiotic(s), successively suctioned so as to be analyzed by flow cytometry, the performing of a step of adjustment of the optical density of the enriched and decomplexified sample being carried out before the introduction of the antibiotic(s).

Advantageously, the step of analysis of susceptibility of the sample to one or more antibiotic(s) is carried out by flow cytometry analysis of a shift in the fluorescence signal between microorganisms sensitive, intermediate or resistant to the antibiotics tested with the enriched and decomplexified sample. For this, a step of labeling with a fluorescent label which is non-specific or specific for the one or more species of interest must be carried out. This step can be carried out before the incubation step, during the incubation step or following the incubation step. This labeling step can last approximately 15 minutes, at a temperature of 35° C. so as to leave the one or more species of interest sufficiently in the presence of the label(s) and to thus make them detectable.

The performing of a step of labeling with a fluorescent label which is non-specific or specific for the one or more species of interest can be carried out using: labels for nucleic acids, such as propidium iodide, SYTO9 or else SYBR® Green, labels for membrane potential, such as DiBAC or else fluorescein derivatives coupled to enzymes specific for the microorganisms of interest, which, once cleaved inside the microorganism, become fluorescent.

By way of example, other labels can be used from the list below:
labels for nucleic acids: TOTO-3, SYTOX Green, Ethidium Bromide, Hoechst 33258/33342, SYTO 13, Mithramycin, Pyronin Y,
protein labels: FITC, Texas Red (sulforhodamine isothiocyanate), Oregon Green isothiocyanate,
cell function labels: Indo-1, Fura-2, Fluor-3,
pH-dependent labels: BCECF, SNARF-1, DIOC6(3),
labels for membrane potential: Oxonol, [DiBAC4(3)], Rhodamine 123, Fun-1,
lipophilic labels: Nile Red,
lectins coupled to fluorescent labels,
oligonucleotides coupled to fluorescent labels,
substrates coupled to fluorochromes,
antibodies coupled to fluorochromes.

This labeling step can be carried out on line, directly following the decomplexification step, by bringing the decomplexified sample into contact with a solution containing fluorescent labels. This bringing into contact can be carried out directly in the outlet orifice containing the decomplexified sample.

Following this labeling step, the flow cytometry analysis step aims to detect the presence of said fluorescent label.

This step is preferentially carried out on line, directly following the labeling step. This step can be carried out by taking the decomplexified sample from the outlet orifice and by introducing it into a flow cytometer or by directly conveying it via a microfluidic device. Advantageously, the buffer solution introduced into the device for carrying out the step of separation by acoustophoresis can be compatible with a flow cytometry analysis step. Preferentially, this buffer solution can comprise fluorescent labels in order to directly carry out the labeling of the species of interest that is (are) contained in the biological sample.

The term "biological sample" is intended to mean a sample of whole blood or of a derivative thereof, such as serum, a sample from a blood culture, or else a sterile or non-sterile, liquid or viscous body fluid sample which may contain one or more species of interest, such as microorganisms. A biological sample can also have a solid or semi-solid matrix, in suspension in a liquid such as a buffer solution. By way of example of sterile body fluids, mention may be made of urine, cerebrospinal fluid and synovial specimens. By way of example of non-sterile body fluids, mention may be made of bronchoalveolar lavages.

The term "sample from a blood culture" is intended to mean a blood sample, brought into contact with a culture medium and incubated for a period of time so as to promote the growth of microorganisms that may be present in the blood sample. The term "positive blood culture" is intended to mean a blood sample brought into contact with a culture medium and incubated for a period of time following which the presence of a microorganism in the blood sample is proven. This presence can generally be confirmed when the concentration in microorganisms in the mixture reaches a threshold, generally of between $10e^7$ and $10e^9$ CFU/ml. Systems sold by the applicant, such as BacT/ALERT® VIRTUO™, are capable of providing positive blood cultures. This system makes it possible to detect the presence of microorganisms in blood samples. For this, a volume of sample is dispensed into a culture bottle containing a liquid culture medium and then placed in an incubator. Various types of bottles make it possible to promote the growth of particular microorganisms. The bottle is monitored during the incubation, said incubation possibly lasting up to 72 h, and a positive growth signal is given if the concentration reaches a predetermined threshold.

Within the meaning of the present invention, the term "microorganism" covers Gram-positive or Gram-negative bacteria, yeasts, molds, amebae and more generally single-cell organisms, invisible to the naked eye, which can be handled and multiplied in the laboratory and which can represent pathogenic agents, in particular pathogenic to humans.

According to one preferred embodiment of the invention, the microorganism is a Gram-negative or Gram-positive bacterium, a yeast or a mold.

By way of example of Gram-positive bacteria, mention may be made of bacteria of the following genera: *Enterococcus, Streptococcus, Lactobacillus, Bifidobacterium, Staphylococcus, Bacillus, Listeria, Clostridium, Mycobacteria, Nocardia, Corynebacteria, Micrococcus* and *Deinococcus*.

By way of example of Gram-negative bacteria, mention may be made of bacteria of the following genera:
*Escherichia*, in particular *Escherichia coli* O157:H7, *Enterobacter, Klebsiella, Salmonella, Proteus, Serratia* and *Campylobacter*.

By way of example of yeasts, mention may be made of the following genera: *Candida, Cryptococcus, Saccharomyces* and *Trichosporon*.

By way of example of molds, mention may be made of the following genera: *Aspergillus, Penicillium, Cladosporium*.

The present invention also relates to various associated microfluidic devices which allow the decomplexification of biological samples, thus allowing the capture and/or analysis of species of interest that is (are) contained or may be contained in the sample.

The present invention also relates to various supports for associated microfluidic devices which allow the decomplexification of biological samples, thus allowing the capture and/or analysis of the biological species that is (are) contained or may be contained in the sample.

The present invention also relates to various connection devices or connectors for associated microfluidic devices which allow the decomplexification of biological samples, thus allowing the analysis of the species of interest that is (are) contained or may be contained in the sample.

Finally, the present invention relates to an air regulation system which can be combined with connection devices or connectors for associated microfluidic devices which allow the decomplexification of biological samples, thus allowing the analysis of the species of interest that is (are) contained or may be contained in the sample.

BRIEF DESCRIPTION OF THE DRAWINGS

The invention, its functionality, its applications and also its advantages will be understood more clearly on reading the present detailed description which follows, given with reference to the figures, in which:

FIG. 4 represents a view from above of a first microfluidic device with two inlet orifices according to the invention, capable of carrying out the process according to the invention, FIG. 5*a* represents a view along section B-B of the microfluidic device according to FIG. 4, FIG. 11 represents a view from above of a fifth microfluidic device with two inlet orifices according to the invention, capable of carrying out the process according to the invention, FIG. 12a represents a partial section along the plane A-A of FIG. 11, FIG. 12b represents a partial section along plane B-B of FIG. 11.

Figure 1:
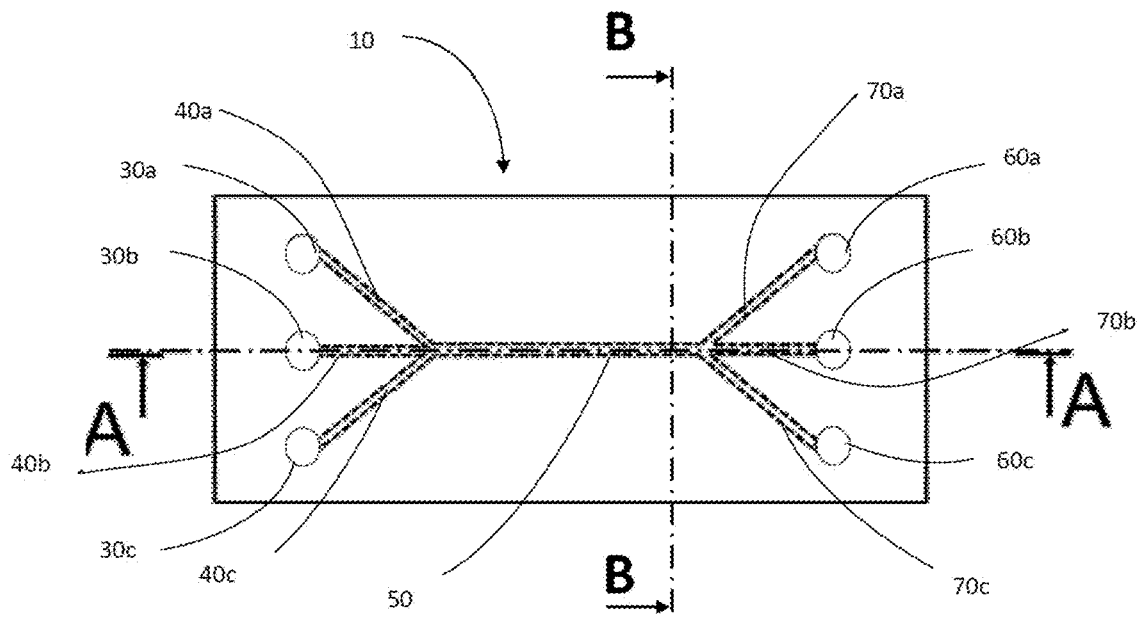
FIG. 1 represents a view from above of a microfluidic device of the prior art, capable of carrying out the process according to the invention.

The aim of the detailed description hereinafter is to disclose the invention in a sufficiently clear and complete manner, in particular with reference to the abovementioned figures, but should not in any case be regarded as limiting the extent of the protection to the particular embodiments which are the subjects of said figures.

Processes for separating particles, cells or molecules in continuous flow using microfluidic devices can make it possible to treat large volumes of sample, this being by continually introducing the sample into the microfluidic device. Another advantage of these techniques is their potential to be integrated upstream or downstream of a step of capture or analysis of the sample, thus performing a routing role and/or acting as a filter in a system for treatment and analysis of a complex biological or chemical sample.

A certain number of forces have been successfully used in microfluidic devices, including inertia, electric and magnetic forces and also mechanical contact forces. Among these various forces applied for separating particles, cells or molecules in microfluidic devices, acoustic forces generated from ultrasonic waves have also been widely used for separating particles of micrometric size in suspension, in order to separate them from their medium and/or other particles. This technique, termed acoustophoresis, enables non-destructive and label-free separation, solely on the basis of the size, the density and the compressibility of particles, cells or molecules.

Acoustophoresis consists of the application of a standing acoustic wave to one or more channels of a microfluidic device, which thus exhibits a pressure profile that is immobile and arranged transversely with respect to the targeted channel. The pressure profile of the standing acoustic waves applied thus varies between high-pressure zones called nodes and low-pressure zones called antinodes.

Conventionally, several fluids of different densities are introduced, via conveying channels, into a microfluidic device so as to flow in laminar fashion (thus without mixing) in the separation channel, facing a piezoelectric ultrasonic transducer. When the transducer is not excited by a control signal, the fluids introduced escape from the separation channel without observing mixing or migration from one fluid to the other. By applying a control signal to the transducer, the particles present in the various fluids will be subjected to the acoustic force thus generated and will move toward the pressure nodes or the antinodes depending on their size, their density and their compressibility. The acoustic force is also called acoustic radiation pressure. The density of the fluids introduced and also their compressibility also have an influence. This migration of the particles in the separation channel thus makes it possible to promote their concentration in certain conveying channels and toward the outlet orifices of the microfluidic device, downstream of the separation channel.

The amplitude of the acoustic radiation generated by the transducer is proportional to that of the control signal applied; however, the maximum effects of the acoustic force are obtained from one and the same control signal when the frequency and the amplitude thereof cause the microfluidic device to resonate. For a configuration with a single pressure node, this resonance frequency is dependent on the width of the separation channel and also on the material of which the device is made. Conventional materials that can be used are glass or silicon, said materials having ideal surfaces for reflecting acoustic waves.

The radiation pressure due to the acoustic wave has a major influence on particles greater than 2 µm in size. Since this pressure is directly proportional to the volume of the particles, a minor change in the radius of the particle rapidly decreases or increases its impact thereon.

Another force is also created by a standing ultrasonic wave in a channel containing a suspension of microparticles. This force is due to the scattering and reflection of the acoustic wave in the fluid and on the particles. The acoustic scattering force is relatively weak and affects especially particles smaller than 2 µm.

An acoustophoresis separation device can thus be created by the use of an ultrasonic acoustic transducer facing a surface of reflection or a second transducer so as to establish a resonant standing wave in the separation channel.

A microfluidic device thus comprises at least two inlet orifices, a separation channel and at least two outlet orifices. The inlet orifices open to the separation channel, while the separation channel opens to the outlet orifices. The device is arranged such that an ultrasonic transducer can be integrated into or attached to a wall of said separation channel. The ultrasonic transducer thus integrated or attached is capable of transmitting mechanical oscillations in multiple acoustic waves acting on the content of the separation channel.

Figure 2A:
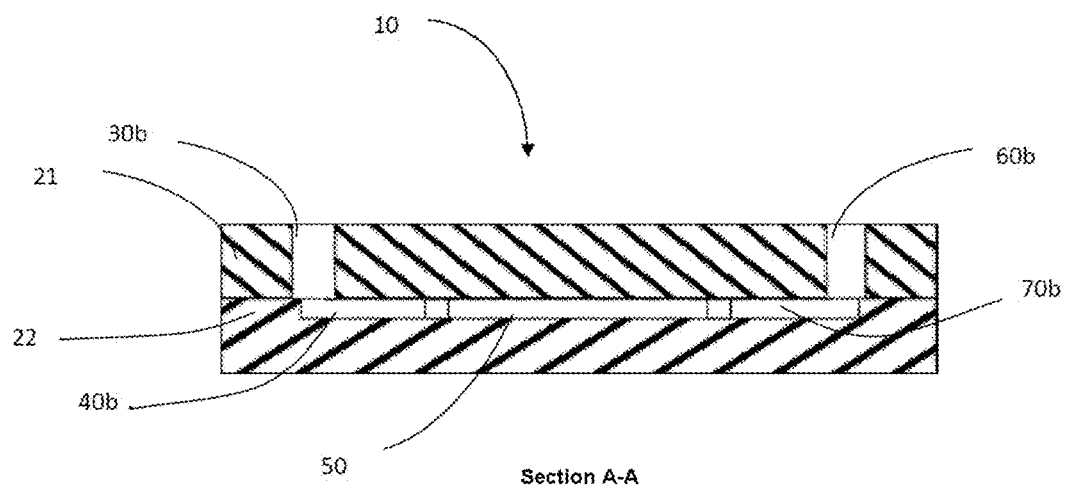
FIG. 2*a* represents a view in longitudinal section of the microfluidic device of the prior art according to the plane of section A-A of FIG. 1.

As represented in FIG. 1 and FIG. 2a, a microfluidic device 10 of the prior art comprises two fluidic parts 21 and 22, the part 21 also being called cover plate and the part 22 also being called separator. The separator and the cover plate are substantially flat, and assembled together so as to form fluidic channels. The separator is microthermally linked to the cover plate so as to produce a device 10 that can be observed by an optical analysis device such as a microscope.

The device is composed of three inlet orifices 30a, 30b, 30c and of three outlet orifices 60a, 60b and 60c connected by a rectilinear separation channel 50, which is 35 mm in length, allowing, during operation of the system, the cells, particles or molecules to become acoustically concentrated in the conveying channel 70b, the axis of which is identical to and in the extension of the axis of the separation channel 50. The cells, particles or molecules are acoustically concentrated in the central channel according to their density, their size and their compressibility.

The three inlet orifices 30a, 30b, 30c, communicate with the separation channel 50 by means of conveying channels respectively 40a, 40b, 40c. The separation channel 50 also communicates with the three outlet orifices 60a, 60b, 60c, by means of conveying channels, respectively 70a, 70b, 70c.

The separator 22 comprises a glass plate 1 mm thick, coated with a layer of chromium and with a layer of photosensitive resin. After development of the photosensitive layer, the glass is etched with hydrofluoric acid (HF) producing conveying and separation channels 125 µm deep, having a width, at the bottom of the channels, of less than 375 µm, and a width of greater than 625 µm in the plane of the separator in contact with the cover plate. The cover plate 21 is pierced so as to produce the inlet and outlet orifices and then thermally bonded with the separator in order to produce a sealed assembly.

The conveying channels of the inlet orifices 40a, 40b, 40c have an angle of respectively 45°, 0° and minus 45° relative to the separation channel in the plane of the separator, so as to slow down the flow rate of the fluids from the conveying channels having an angle of 45° or −45°, 40a, 40c, relative to the separation channel, and to thus promote the appearance of a laminar flow in the separation channel.

Figure 2B:
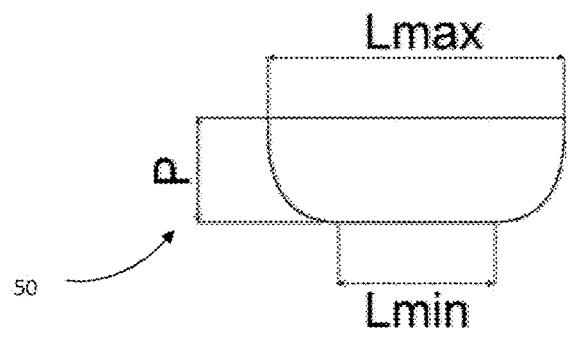
FIG. 2*b* represents a cross section of the separation channel 50 according to the plane of section B-B of FIG. 1.

The standard profile of a conveying or separation channel is represented in FIG. 2b. The channels are D-shaped in the plane perpendicular to the axis of the channel in question, the greatest width being located in the plane in contact with the cover plate when the device is assembled. They thus have a lower width "Lmin" at the bottom of the channels, an upper width "Lmax" in the plane of the separator in contact with the cover plate when the device is assembled, and also a depth "P".

This device of the prior art is capable of carrying out processes for treating biological samples by acoustophoresis such as the process of the invention. For this, all or part of the biological sample to be treated is introduced into the inlet orifices 30a and 30c of the device 10. A buffer solution is introduced into the inlet orifice 30b, the buffer and the sample being introduced at respective flow rates capable of generating a laminar flow in the separation channel. An ultrasonic transducer, such as a piezoelectric transducer, attached to the separation channel is then activated by a control signal, so as to carry out a step of separation of said biological sample by acoustophoresis. This separation makes it possible to promote the concentration of the non-specific particles in the sample, in the outlet orifice 60b of said acoustophoresis device. The decomplexified sample is obtained in the outlet orifices 60a and 60c. The concentrated sample is obtained in the outlet orifice 60b.

The invention also relates to various microfluidic devices which allow the treatment of biological samples by acoustophoresis. These various devices are also capable of advantageously carrying out the process according to the invention. These devices are particularly advantageous to use with the process according to the invention since they make it possible to achieve sample preparation flow rates which are higher than prior art devices while at the same time ensuring a degree of decomplexification which is equal to or greater than those observed in the prior art for biological samples such as primary blood samples or sterile body fluids incubated in culture medium.

The inlet orifices and the shape of the conveying channels communicating with the inlet orifices can advantageously be optimized in order to accept a sedimentation of the non-specific particles, aggregates (of lipids or of erythrocytes) or debris at the inlets of the microfluidic device without risk of blocking the channels of the device. In this respect, the part of each conveying channel opposite each inlet orifice capable of receiving the biological sample can have a cavity with a depth greater than the general depth of the conveying channel. Advantageously, the cavity opposite the inlet orifice is two to three times deeper than the conveying channel connected to said orifice. This cavity makes it possible to create a zone of slowed or zero speed of the sample introduced, promoting sedimentation of the non-specific particles. The device thus formed exhibits better tolerance to blockages linked to the introduction of non-specific particles of large size and high density.

For each of these embodiments, the separator can be made of silicon, ceramic or glass, the channels being obtained by chemical or physical etching (e.g. sanding). The separator can also be made of flexible and thin polymer material such as polydimethylsiloxane (PDMS), polypropylene or a polymer/silicone bicompound (for example a polystyrene with a flexible film of silicone or of PDMS in order to ensure air-free coupling of the piezoelectric transducers on the wall of the device), the channels then being obtained by molding. The advantage of the use of a flexible and thin polymer material is to be able to produce a device at very low cost, allowing its routine use as a consumable in processes for preparing biological samples by acoustophoresis such as the process according to the invention. Another advantage is that of not requiring any adhesive or coupling gel between the piezoelectric transducer(s) and the walls of the separation channel.

For each of these embodiments, each inlet or outlet orifice can form a reservoir so as to be able to carry out sample storage operations and also depositing and pipetting operations. A step of incubation of the sample can also be carried out by attaching a heating means at an orifice. Advantageously, an orifice can be made in a transparent or translucent material, so as to be able to directly carry out a reading of the optical density of the sample that it contains.

For each of these embodiments, each device can be used alone or in parallel so as to be able to treat a volume of biological sample at a higher flow rate. Indeed, if the flow rate of introducing the fluids into one and the same separation channel is increased, the degree of decomplexification of the sample can rapidly decrease, since the particles do not have time to be separated by the acoustic wave due to too short a residence time in the device. Furthermore, if the size of the channels, in particular of the separation channel, is increased, in the hope of also being able to increase the treatment flow rate, the amplitude of excitation (of the control signal) of the piezoelectric transducer(s) required for good separation of the particles will have to be much greater since the resonance frequency will be reduced and consequently the radiation pressure on the particles to be focused at the center of the separation channel. However, if the ultrasonic transducer is excited at a greater amplitude, it can cause local heating in the separation channel. This heating is not desirable since it can cause degradation of the device and also of the viability of the particles, cells or molecules of interest present in the separation channel. Furthermore, this heating can cause a change in density of the buffer used, which can modify the propagation of the acoustic waves in the channel and disrupt the separation step. As a result, the devices according to the invention, used alone or in parallel, make it possible to obtain separation/decomplexification flow rates that are equal to or greater than the prior art while at the same time guaranteeing the viability of the particles, cells or molecules of interest treated.

Thus, the separation channels of the various devices according to the invention have a length that can be between 35 mm and 80 mm. The lower widths of the separation channel are for example between 300 µm and 375 µm, the upper widths are for example between 550 µm and 625 µm. The depth of the separation channel can be between 100 µm and 150 µm, preferentially 125 µm. The various devices according to the invention are suitable for use with control signals of attached ultrasonic transducer(s) having a frequency of between 300 kHz and 10 MHz, preferentially of 1.3 MHz, alternatively of 1.44 MHz for the creation of a single pressure node at the center of the channel. These various frequency values make it possible to obtain central focusing (a single pressure node in the separation channel) exhibiting non-specific particles focused in the outlet orifice in the extension of the axis of the separation channel or to promote the concentration of these non-specific particles in one of the outlet orifices. Various resonance frequencies can be observed for one and the same device due to the appearance of several pressure nodes in the width of the separation channel in multiples of a quarter of the wavelength (nλ/4). Slight variations of approximately 30 kHz around the resonance frequency can also make it possible to obtain better resonance of the device, this frequency being dependent on the quality of production of the channels of the device.

The amplitude of the control signal is between 0.1 V and 100 V, preferentially 38 V. For control signal amplitudes greater than 38 V, it may be desirable to use a cooling device attached to the ultrasonic transducer(s) in order to prevent degradation of the device and/or damage to the viability of the particles, cells or molecules present in the separation channel. Peltier blocks or fans can constitute such cooling devices. Advantageously, the cooling device is temperature-controlled in order to regulate the temperature in the vicinity of the ultrasonic transducer.

For each of these embodiments, the conveying channels of the inlet orifices used to introduce the biological sample have an angle of between 30 and 60°, preferentially of 45° relative to the separation channel in the plane of the separator. This angle can easily be adjusted by those skilled in the art so as to more or less slow down the flow rate of introduction of the fluid into the separation channel, and to thus ensure the appearance of a laminar flow of the fluids in this channel. These conveying channels are called side channels since they make it possible to introduce the fluid in the direction of the walls of the separation channel.

For each of these embodiments, the conveying channels to the outlet orifices used to recover or reintroduce the decomplexified sample have an angle of between 30 and 60°, preferentially of 45° relative to the separation channel in the plane of the separator. This angle can easily be adjusted by those skilled in the art so as to more or less slow down the flow rate of suction of the fluid out of the separation channel, and to thus ensure the appearance of a laminar flow of the fluids in this channel. These conveying channels are also called side channels since they make it possible to suction the fluid circulating along the walls of the separation channel.

The conveying channels of which the axis or axes is or are identical to the axis of the separation channel are called central channels. These channels transport the concentrated sample.

Furthermore, the cross sections of the conveying channels of the inlet and outlet orifices can be adjusted. In particular, the cross sections of the conveying channels of the side outlet orifices (in which the decomplexified sample is found) relative to the cross section of the conveying channel of the central outlet orifice (in which a maximum of non-specific particles is found) can be adjusted in order to guarantee better focusing at the level of the outlet branching between these channels. In this zone, at the junction of the separation channel and the conveying channels to the outlet orifices, the resonance is not very effective (since there are no longer side walls at the branching) for a short transient time. This results in a partial loss of focusing of the non-specific particles. In the case of the device illustrated in FIG. 1, the adjustment of the ratios of the cross sections between the channels 70a or 70c and 70b can thus make it possible to minimize the losses of microorganisms or to improve the degree of concentration of the non-specific particles or debris in the central conveying channel 70b.

A first embodiment of a device according to the invention is represented in FIGS. 4 and 5a. This device 200 comprises two inlet orifices 230a, 230b, a separation channel 250 and at least two outlet orifices 260a, 260b. The device 200 comprises two fluidic parts, a separator 222 and a cover plate 221, which are substantially planar. These two parts are assembled hermetically. The inlet orifices open to the separation channel, while the separation channel opens to the outlet orifices by means of conveying channels. Thus, the separation channel 250 opens to the orifice 230a via the conveying channel 240a, to the orifice 230b via the conveying channel 240b, to the orifice 260a via the conveying channel 270a, and to the orifice 260b via the conveying channel 270b. In a first alternative of implementation of this first embodiment, the device is arranged such that at least one ultrasonic transducer can be integrated into or attached to a wall of said separation channel. The ultrasonic transducer thus integrated or attached is capable of transmitting mechanical oscillations in multiple acoustic waves which can act on the content of the separation channel.

In a second alternative implementation of this first embodiment, the device comprises two recesses 290a, 290b, made along the separation channel 250, in the separator 222, and capable of each receiving an ultrasonic transducer. This embodiment makes it possible to obtain a standing wave in a separator made of a material that barely reflects acoustic waves, the material being flexible and thin such as plastic, polymer or silicone materials. A silicone preferentially used is polydimethylsiloxane (PDMS). Preferentially, each ultrasonic transducer comprises a quarter-wave adapter plate, the acoustic impedance of which is calculated to minimize the energy losses, and thus the heating, between the ultrasonic transducer and the walls of the device. This plate of resin covering the piezoelectric transducer(s) (made by casting and polymerization) is defined so as to have an intermediate acoustic impedance between the acoustic impedance of the material used to produce the device and the acoustic impedance of the piezoelectric transducer(s).

Preferentially, the cover plate 221 is made of polydimethylsiloxane (PDMS) or of molded plastic such as polycarbonate (PC) poly(methyl methacrylate) (PMMA), polypropylene (PP), polystyrene (PS), acrylonitrile butadiene styrene (ABS), cyclic olefin copolymer (COC), cyclic olefin polymer (COP) or polyoxymethylene (POM).

This device 200 is capable of carrying out processes for preparing biological samples by acoustophoresis such as the process according to the invention. For this, all or part of the biological sample to be treated is introduced into the inlet orifice 230a of the device 200. A buffer solution is introduced into the inlet orifice 230b, the buffer and the sample being introduced at respective flow rates capable of generating a laminar flow in the separation channel. An ultrasonic transducer, such as a piezoelectric transducer, attached to the separation channel is then activated by a control signal, so as to carry out a step of separation of said biological sample by acoustophoresis. This separation makes it possible to promote the concentration of the non-specific particles, such as formed elements of the blood, present in the sample, in the outlet orifice 260b of said acoustophoresis device. The decomplexified sample is obtained in the outlet orifice 260a. The non-specific particles are thus transferred into the buffer solution introduced into the inlet 230b. The concentrated sample is thus obtained in the outlet orifice 260b.

Figure 5B:
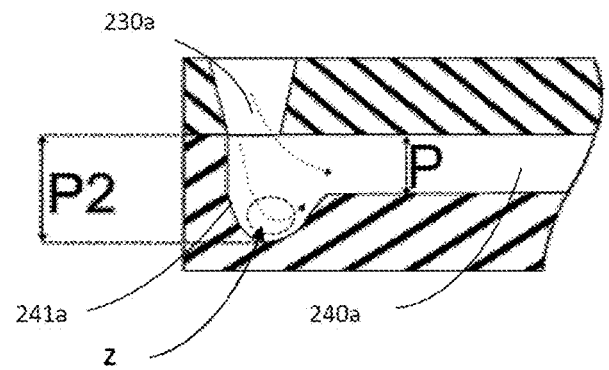
FIG. 5*b* represents one embodiment of an inlet orifice viewed along section A-A of an inlet orifice of the microfluidic device according to FIG. 4.

An alternative for producing the inlet orifice 230a is presented in FIG. 5b. The inlet orifice 230a in this case has a frustoconical shape but can also be cylindrical depending on the introduction means chosen. The shape of the conveying channel 240a, opposite the orifice 230a, is modified so as to comprise a cavity 241a of greater depth than the general depth of the conveying channel 240a. This cavity thus has a depth P2 with P2 between two and three times the depth P of the conveying channel. This cavity makes it possible to create a zone of slowed or zero speed (Z) of the sample introduced, promoting the sedimentation of the non-specific particles contained in the sample. The device thus formed exhibits better tolerance to blockages associated with the introduction of non-specific particles of large size and high density.

Figure 6A:
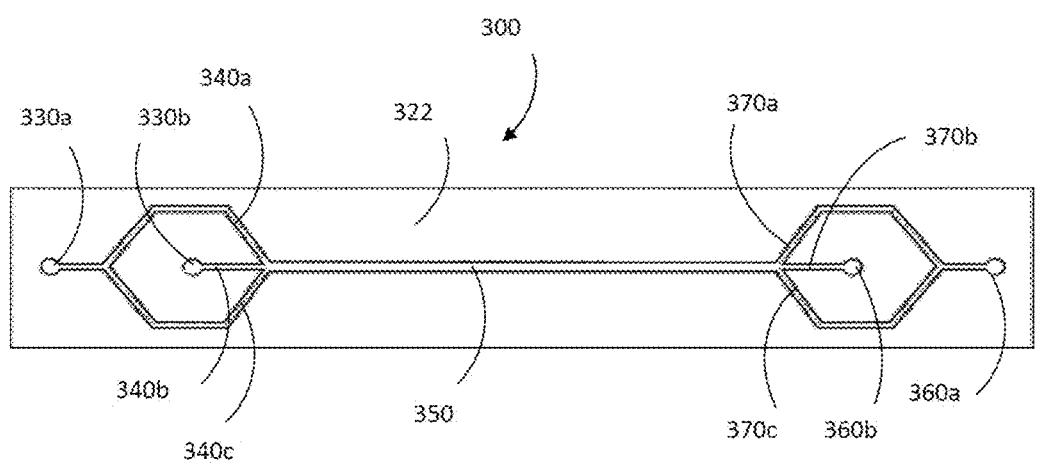
FIG. 6*a* represents a view from above of a second microfluidic device with two inlet orifices according to the invention, capable of carrying out the process according to the invention.

As represented in FIG. 6a, the invention also relates to a second embodiment of a device 300 comprising two fluidic parts, a separator 322 and a cover plate (not represented), these two parts being substantially planar. These two parts are assembled hermetically. Channels are made in the separator 322. The device 300 comprises two inlet orifices 330a, 330b, in fluidic communication with at least one separation channel 350 by means of conveying channels respectively 340a, 340c for the orifice 330a and 340b for the orifice 330b. The separation channel 350 is also in fluidic communication with two outlet orifices 360a, 360b, by means of conveying channels, respectively 370a and 370c for the orifice 360a and 370b for the orifice 360b. This configuration makes it possible to simplify the fluidic connection since it has only two inlet orifices and two outlet orifices. Likewise, the collection of the decomplexified sample can be carried out in an outlet orifice or a single collection tube. Furthermore, since the conveying channels 370a and 370c to the outlet orifice 360a are directly connected by etching of the channels on the device, the equilibration of the pressure drops at the branching of the conveying channels to the outlet orifices is significantly improved. A minimal difference in pressure drop (linked to a difference in connection of the outlet tubes on the device) can lead to a disruption of the focusing and thus considerable degradation of the decomplexification performance levels.

The device 300 is arranged such that an ultrasonic transducer, not represented, can be integrated into or attached to a wall of said separation channel 350. The ultrasonic transducer thus integrated or attached is capable of transmitting mechanical oscillations in multiple acoustic waves that can act on the content of the separation channel and generate therein a standing acoustic wave. An alternating current generator combined with a signal amplifier (which are not represented), can be electrically connected to the transducer in order to generate a signal for control of the transducer, the frequency, waveform and amplitude of which are known.

In one particular embodiment of the device 300, the separator 322 is made of a glass plate 1 mm thick, coated with a layer of chromium and with a layer of photosensitive resin. After development of the photosensitive layer, the glass is etched with hydrofluoric acid (HF). The conveying channels 340a and 340c, 370a and 370c have a depth P of 125 μm, a lower width Lmin, at the bottom of the channels, of 300 μm, and an upper width Lmax of 550 μm in the plane of the separator in contact with the cover plate. The conveying channels 340b and 370b and also the separation channel 350 have a depth P of 125 μm, a lower width Lmin, at the bottom of the channels, of 375 μm, and an upper width Lmax of 625 μm in the plane of the separator in contact with the cover plate. The cover plate is pierced so as to produce the inlet and outlet orifices and then thermally bonded with the separator in order to produce a sealed assembly. The conveying channels of the inlet orifices 340a, 340b have an angle of respectively 45°, 0° and minus 45° relative to the separation channel 350 in the plane of the separator, so as to slow down the flow rate of the fluids originating from the conveying channels having an angle of 45° or −45°, 340a, 340b, relative to the separation channel. The rectilinear separation channel 350 has a length of 80 mm, allowing the cells, particles or molecules to become acoustically concentrated in the conveying channel 370b during the operation of the system. The axis of the conveying channel 370b is identical to the axis of the separation channel. The cells, particles or molecules are acoustically concentrated in the central channel 370b, according to their density, their size and their compressibility.

Alternatively, the separator 322 of the device 300 comprises two recesses (not represented) made along the separation channel 350, and capable of each receiving an ultrasonic transducer (not represented). This embodiment makes it possible to obtain a standing wave in the separator 322 if the latter is made of a material that does not reflect acoustic waves very much, the material being flexible and thin such as plastic, polymer or silicone materials. A silicone preferentially used is polydimethylsiloxane (PDMS). Preferentially, each ultrasonic transducer comprises a quarter-wave adapter plate of which the acoustic impedance is calculated to minimize the energy losses, and thus the heating, between the ultrasonic transducer and the walls of the device.

Preferentially, the cover plate (not represented) is made of PDMS or of molded plastic such as polycarbonate (PC), poly(methyl methacrylate) (PMMA), polypropylene (PP), polystyrene (PS), acrylonitrile butadiene styrene (ABS), cyclic olefin copolymer (COC), cyclic olefin polymer (COP) or polyoxymethylene (POM).

This device 300 is capable of carrying out processes for preparing biological samples by acoustophoresis such as the process according to the invention. For this, all or part of the biological sample to be treated is introduced into the inlet orifice 330a of the device 300. A buffer solution is introduced into the inlet orifice 330b, the buffer and the sample being introduced at respective flow rates capable of generating a laminar flow in the separation channel. An ultrasonic transducer, such as a piezoelectric transducer, attached to the separation channel is then activated by a control signal, so as to carry out a step of separation of said biological sample by acoustophoresis. This separation makes it possible to promote the concentration of the non-specific particles, such as formed elements of the blood, present in the sample, in the outlet orifice 360b of said acoustophoresis device. The decomplexified sample is obtained in the outlet orifice 360a. The concentrated sample is obtained in the outlet orifice 360b.

Figure 6B:
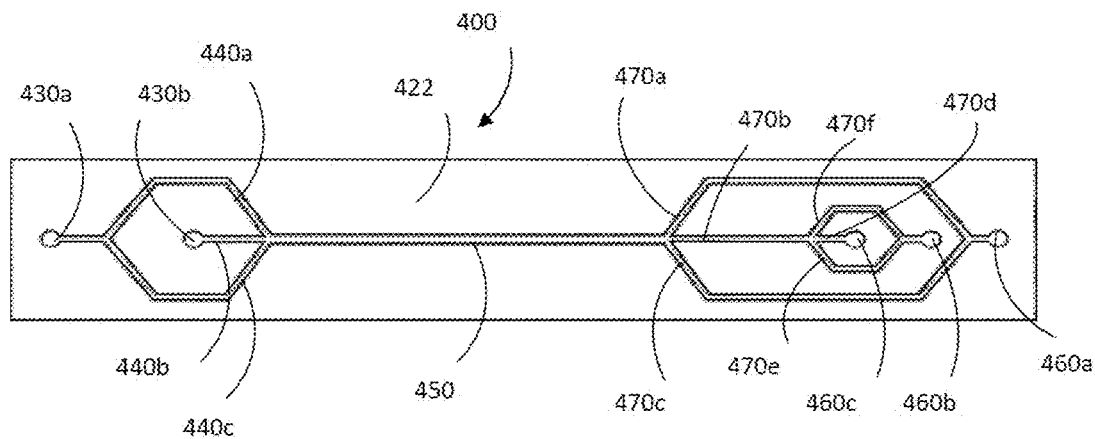
FIG. 6*b* represents a view from above of a third microfluidic device with two inlet orifices according to the invention, capable of carrying out the process according to the invention.

As represented in FIG. 6b, the invention also relates to a device 400 comprising two fluidic parts, a separator 422 and a cover plate (not represented), these two parts being substantially planar. These two parts are assembled hermetically. Fluidic channels are made in the separator 422. The device 400 comprises two inlet orifices 430a, 430b, in fluidic communication with at least one separation channel 450 by means of conveying channels, respectively 440a, 440c, for the orifice 430a and 440b for the orifice 430b. The separation channel 450 is also in fluidic communication with three outlet orifices 460a, 460b, 460c, by means of conveying channels, respectively 470a and 470c for the orifice 460a, 470b and 470d for the orifice 460c, and 470b, 470f and 470e for the outlet orifice 460b. The device 400 is arranged such that an ultrasonic transducer, not represented, can be integrated into or attached to a wall of said separation channel 450. The ultrasonic transducer thus integrated or attached is capable of transmitting mechanical oscillations in multiple acoustic waves that can act on the content of the separation channel and generate therein a standing acoustic wave. A function generator combined with a signal amplifier, which are not represented, can be electrically connected to the transducer in order to generate a transducer control signal of which the frequency, the waveform and the amplitude are known. The conveying channel 470b, placed in the extension of the separation channel 450, makes it possible to carry out a second step of separation of the non-specific particles that may remain in the biological sample.

In one particular embodiment of the device 400, the separator 422 is made of a glass plate 1 mm thick, coated with a layer of chromium and with a layer of photosensitive resin. After development of the photosensitive layer, the glass is etched with hydrofluoric acid (HF). The conveying channels 440a, 440c, 470a, 470c, 470e and 470f have a depth P of 125 µm, a lower width Lmin, at the bottom of the channels, of 300 µm, and an upper width Lmax of 550 µm in the plane of the separator in contact with the cover plate. The conveying channels 440b, 470b and 470d and also the separation channel 450 have a depth P of 125 µm, a lower width Lmin, at the bottom of the channels, of 375 µm, and an upper width Lmax of 625 µm in the plane of the separator in contact with the cover plate. The cover plate is pierced so as to make the inlet and outlet orifices and then thermally bonded with the separator in order to produce a sealed assembly. The conveying channels of the inlet orifices 440a, 440b, 440c have an angle of respectively 45°, 0° and minus 45° relative to the separation channel 450 in the plane of the separator, so as to slow down the flow rate of the fluids originating from the conveying channels having an angle of 45° or −45°, 440a, 440c, relative to the separation channel. The rectilinear separation channel 450 has a length of 80 mm, making it possible, during operation of the system, for the cells, particles or molecules to become acoustically concentrated in the conveying channel 470b then 470d, the axes of which are identical to the axis of the separation channel.

Alternatively, the separator 422 of the device 400 comprises two recesses (not represented) made along the separation channel 450 and capable of each receiving an ultrasonic transducer (not represented). This embodiment makes it possible to obtain a standing wave in the separator 422 if the latter is made of a material which does not reflect acoustic waves very much, the material being flexible and thin such as plastic, polymer or silicone materials. A silicone preferentially used is polydimethylsiloxane (PDMS). Preferentially, each ultrasonic transducer comprises a quarter-wave adapter plate of which the acoustic impedance is calculated so as to minimize the energy losses, and thus the heating, between the ultrasonic transducer and the walls of the device.

Preferentially, the cover plate (not represented) is made of PDMS or of molded plastic such as polycarbonate (PC), poly(methyl methacrylate) (PMMA), polypropylene (PP), polystyrene (PS), acrylonitrile butadiene styrene (ABS), cyclic olefin copolymer (COC), cyclic olefin polymer (COP) or polyoxymethylene (POM).

This device 400 is capable of carrying out the processes for preparing biological samples by acoustophoresis such as the process according to the invention. For this, all or part of the biological sample to be treated is introduced into the inlet orifice 430a of the device 400. A buffer solution is introduced into the inlet orifice 430b, the buffer and the sample being introduced at respective flow rates capable of generating a laminar flow in the separation channel. An ultrasonic transducer, such as a piezoelectric transducer, attached to the separation channel is then activated by a control signal, so as to carry out a step of separation of said biological sample by acoustophoresis. This separation makes it possible to promote the concentration of the non-specific particles, such as formed elements of the blood, present in the sample, in the conveying channel 470b of said acoustophoresis device. The decomplexified sample is obtained in the outlet orifice 460a. A second step of separation of said biological sample by acoustophoresis is carried out on the part resulting from the first separation, the concentrated sample, in the channel 470*b*. This separation makes it possible to promote the concentration of the non-specific particles, such as formed elements of the blood, present in the concentrated sample, in the outlet orifice 460*c* of said acoustophoresis device. The sample decomplexified a second time is obtained in the outlet orifice 460*b*. The collection and the mixing of the decomplexified samples from the outlet orifices 460*a* and 460*b* make it possible to increase the collection yield of the microorganisms present in the biological sample. This is because the microorganisms entrained with the non-specific particles during the first separation in the channel 470*b* are capable of being separated by acoustophoresis in this channel 470*b* and of thus being capable of being collected following this second separation in the orifice 460*b*.

The relative position and the length of the second separation channel 470*b* with respect to the main separation channel 450 is chosen according to the desired applications, performance levels and flow rates.

Figure 6C:
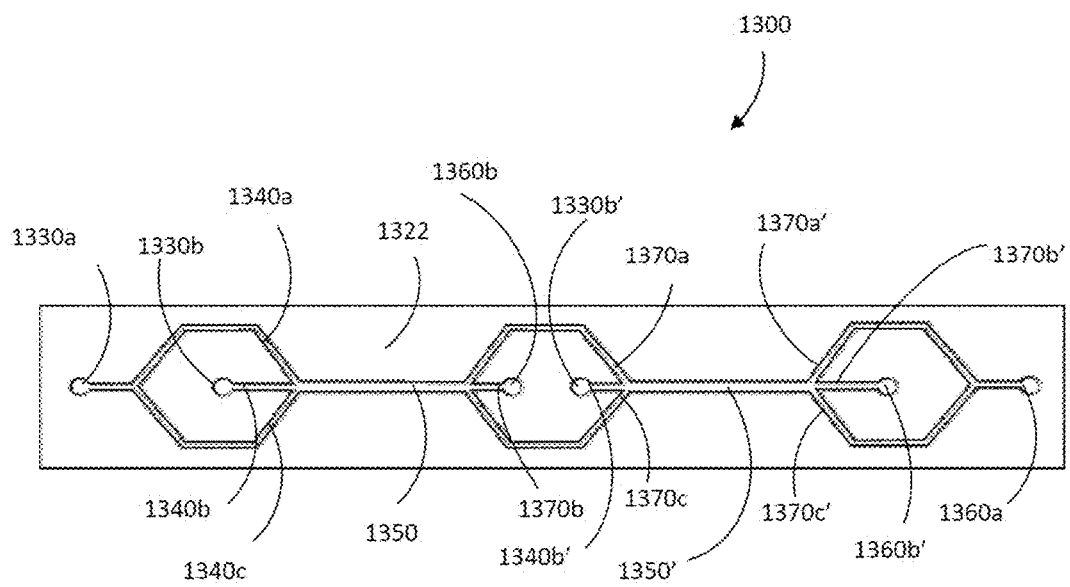
FIG. 6*c* represents a view from above of a fourth microfluidic device with three inlet orifices according to the invention, capable of carrying out the process according to the invention.

As represented in FIG. 6*c*, the invention also relates to a fourth embodiment of a device 1300 comprising two fluidic parts, a separator 1322 and a cover plate (not represented), these two parts being substantially planar. These two parts are assembled hermetically. Channels are made in the separator 1322. The device 1300 comprises two inlet orifices 1330*a*, 1330*b*, in fluidic communication with a first separation channel 1350 by means of conveying channels, respectively 1340*a*, 1340*c* for the orifice 1330*a* and 1340*b* for the orifice 1330*b*. The separation channel 1350 is in fluidic communication with an outlet orifice 1360*b*, by means of a conveying channel 1370*b*. The separation channel 1350 is also in fluidic communication with a second separation channel 1350' by means of two conveying channels 1370*a* and 1370*c*. The second separation channel 1350' is in fluidic communication with an outlet orifice 1360*b'*, by means of a conveying channel 1370*b'* and in fluidic communication with an outlet orifice 1360*a*, by means of two conveying channels 1370*a'* and 1370*c'*.

The device 1300 also comprises an inlet orifice 1330*b'*, in fluidic communication with the second separation channel 1350' via a conveying channel 1340*b'*.

The device 1300 is arranged such that one or more ultrasonic transducers, not represented, can be integrated into or attached to a wall of said separation channels 1350 and 1350'. The ultrasonic transducer(s) thus integrated or attached is (are) capable of transmitting mechanical oscillations in multiple acoustic waves that can act on the content of the separation channels and generate therein a standing acoustic wave. An alternating current generator combined with a signal amplifier, which are not represented, can be electrically connected to the transducer(s) in order to generate a control signal of which the frequency, the waveform and the amplitude are known.

This configuration makes it possible to improve the purity of the decomplexified sample. Indeed, after having concentrated the non-specific particles toward the outlet orifice 1360*b*, the decomplexified sample is injected into the second separation channel 1350' via the channels 1370*a* and 1370*c*. The decomplexified sample is then separated a second time from the non-specific particles that may still be present, said particles being in the orifice 1360*b'*. The sample decomplexified a second time is obtained in the outlet orifice 1360*a*.

In one particular embodiment of the device 1300, the separator 1322 is made of a glass plate 1 mm thick, coated with a layer of chromium and with a layer of photosensitive resin. After development of the photosensitive layer, the glass is etched with hydrofluoric acid (HF). The conveying channels 1340*a* and 1340*c*, 1370*a*, 1370*c*, 1370*a'* and 1370*c'* have a depth P of 125 µm, a lower width Lmin, at the bottom of the channels, of 300 µm, and an upper width Lmax of 550 µm in the plane of the separator in contact with the cover plate. The conveying channels 1340*b*, 1340*b'*, 1370*b* and 1370*b'* and also the separation channels 1350 and 1350' have a depth P of 125 µm, a lower width Lmin, at the bottom of the channels, of 375 µm, and an upper width Lmax of 625 µm in the plane of the separator in contact with the cover plate. The cover plate is pierced so as to make the inlet and outlet orifices and then thermally bonded with the separator in order to produce a sealed assembly.

The conveying channels of the inlet orifices 1340*a*, 1340*b* have an angle of respectively 45°, 0° and minus 45° relative to the separation channel 1350 in the plane of the separator, so as to slow down the flow rate of the fluids originating from the conveying channels having an angle of 45° or −45°, 1340*a*, 1340*c*, relative to the separation channel 1350. The rectilinear separation channel 1350 has a length of 19.5 mm, allowing the cells, particles or molecules to become acoustically concentrated in the conveying channel 1370*b* during operation of the system. The axis of the conveying channel 1370*b* is identical to the axis of the separation channel.

The conveying channels 1370*a*, 1370*b*, 1340*b'* have an angle of respectively 45°, 0° and minus 45° relative to the separation channel 1350' in the plane of the separator, so as to slow down the flow rate of the fluids originating from the conveying channels having an angle of 45° or −45°, 1340*a*, 1340*c*, relative to the second separation channel 1350'. The rectilinear second separation channel 1350' has length of 19.5 mm, allowing the cells, particles or molecules to become acoustically concentrated in the conveying channel 1370*b'* during operation of the system. The axis of the conveying channel 1370*b'* is identical to the axis of the separation channel 1350'. The cells, particles or molecules are acoustically concentrated in the central channel 1370*b'*, according to their density, their size and the compressibility.

Alternatively, the separator 1322 of the device 1300 comprises four recesses (not represented) made along the separation channels 1350 and 1350', and capable of each receiving an ultrasonic transducer (which are not represented). This embodiment makes it possible to obtain a standing wave in the separator 1322 if the latter is made of a material which does not reflect acoustic waves very much, the material being flexible and thin such as plastic, polymer or silicone materials. A silicone preferentially used is polydimethylsiloxane (PDMS). Preferentially, each ultrasonic transducer comprises a quarter-wave adapter plate of which the acoustic impedance is calculated so as to minimize the energy losses, and thus the heating, between the ultrasonic transducer and the walls of the device.

Preferentially, the cover plate (not represented) is made of PDMS or of molded plastic such as polycarbonate (PC), poly(methyl methacrylate) (PMMA), polypropylene (PP), polystyrene (PS), acrylonitrile butadiene styrene (ABS), cyclic olefin copolymer (COC), cyclic olefin polymer (COP) or polyoxymethylene (POM).

This device 1300 is capable of carrying out processes for preparing biological samples by acoustophoresis such as the process according to the invention. For this, all or part of the biological sample to be treated is introduced into the inlet orifice 1330*a* of the device 1300. A buffer solution is introduced into the inlet orifices 1330*b* and 1330*b'*, the buffers and the sample being introduced at respective flow rates capable of generating a laminar flow in the separation channels 1350 and 1350'. One or more ultrasonic transducer(s) attached to the separation channels is (are) then activated by a control signal, so as to carry out two successive steps of separation of said biological sample by acoustophoresis. This separation makes it possible to promote a first time the concentration of the non-specific particles, present in the sample, in the outlet orifice 1360b. Following this first separation, a second separation makes it possible to promote the concentration of the non-specific particles a second time, such as food debris still present in the decomplexified sample originating from the channels 1370a and 1370c, in the outlet orifice 1360b'. The sample decomplexified a second time and having an improved purity is obtained in the outlet orifice 1360a.

The relative position and the length of the second separation channel 1350' with respect to the main separation channel 1350' are chosen according to the desired applications, performance levels and flow rates. Advantageously, two buffer solutions of different type or density are introduced into the inlet orifices 1330b and 1330b'.

Figure 6D:
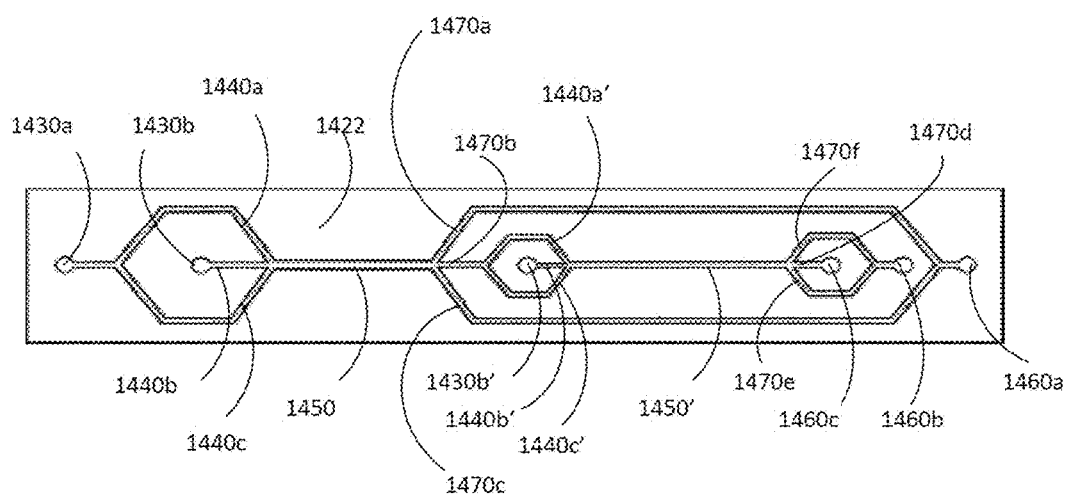
FIG. 6d represents a view from above of a fifth microfluidic device with three inlet orifices according to the invention, capable of carrying out the process according to the invention.

As represented in FIG. 6d, the invention also relates to a fifth device 1400 comprising two fluidic parts, a separator 1422 and a cover plate (not represented), these two parts being substantially planar. These two parts are assembled hermetically. Fluidic channels are made in the separator 1422. The device 1400 comprises two inlet orifices 1430a, 1430b, in fluidic communication with a first separation channel 1450 by means of conveying channels respectively 1440a, 1440c for the orifice 1430a and 1440b for the orifice 1430b.

The first separation channel 1450 is also in fluidic communication with an outlet orifice 1460a, by means of conveying channels 1470a and 1470c.

The first separation channel 1450 is finally in fluidic communication with the second separation channel 1450', by means of conveying channels 1440a' and 1440c'.

The device 1400 also comprises an inlet orifice 1430b', in fluidic communication with the second separation channel 1450 via the conveying channel 1440b'.

The second separation channel 1450' is also in fluidic communication with two outlet orifices 1460b, 1460c, by means of conveying channels, respectively 1470d for the orifice 1460c; 1470e and 1470f for the outlet orifice 1460b.

The device 1400 is arranged such that one or more ultrasonic transducer(s), not represented, can be integrated into or attached to a wall of said separation channels 1450 and 1450'. The ultrasonic transducer(s) thus integrated or attached is (are) capable of transmitting mechanical oscillations in multiple acoustic waves that can act on the content of the separation channels and generate therein a standing acoustic wave. An alternating current generator combined with a signal amplifier, not represented, can be electrically connected to the transducer(s) in order to generate a control signal of which the frequency, the waveform and the amplitude are known.

In one particular embodiment of the device 1400, the separator 1422 is made of a glass plate 1 mm thick, coated with a layer of chromium and with a layer of photosensitive resin. After development of the photosensitive layer, the glass is etched with hydrofluoric acid (HF). The conveying channels 1440a, 1440c, 1470a, 1470c, 1470e and 1470f have a depth P of 125 µm, a lower width Lmin, at the bottom of the channels, of 300 µm, and an upper width Lmax of 550 µm in the plane of the separator in contact with the cover plate. The conveying channels 1440b, 1470b and 1470d and also the separation channels 1450 and 1450' have a depth P of 125 µm, a lower width Lmin, at the bottom of the channels, of 375 µm, and an upper width Lmax of 625 µm in the plane of the separator in contact with the cover plate. The cover plate is pierced so as to make the inlet and outlet orifices and then thermally bonded with the separator in order to produce a sealed assembly. The conveying channels 1440a, 1440c have an angle of respectively 45° and minus 45° relative to the separation channel 1450 in the plane of the separator, so as to slow down the flow rate of the fluids originating from these conveying channels. In the same way, the conveying channels 1440a', 1440c' have an angle of respectively 45° and minutes 45° relative to the separation channel 1450' in the plane of the separator.

The rectilinear separation channels 1450 and 1450' have a length of 22.5 mm allowing, during operation of the system, the cells, particles or molecules to become acoustically concentrated in the conveying channel 1470b then 1470d, the axes of which are identical to the axes of the separation channels.

Alternatively, the separator 1422 of the device 1400 comprises four recesses (not represented) made along the separation channels 1450 and 1450', and capable of each receiving an ultrasonic transducer (which are not represented). This embodiment makes it possible to obtain a standing wave in the separator 1422 if the latter is made of a material which does not reflect acoustic waves very much, the material being flexible and thin such as plastic, polymer or silicone materials. A silicone preferentially used is polydimethylsiloxane (PDMS). Preferentially, each ultrasonic transducer comprises a quarter-wave adapter plate of which the acoustic impedance is calculated so as to minimize the energy losses, and thus the heating, between the ultrasonic transducer and the walls of the device.

Preferentially, the cover plate (not represented) is made of PDMS or of molded plastic such as polycarbonate (PC), poly(methyl methacrylate) (PMMA), polypropylene (PP), polystyrene (PS), acrylonitrile butadiene styrene (ABS), cyclic olefin copolymer (COC), cyclic olefin polymer (COP) or polyoxymethylene (POM).

This device 1400 is capable of carrying out processes for preparing biological samples by acoustophoresis such as the process according to the invention. For this, all or part of the biological sample to be treated is introduced into the inlet orifice 1430a of the device 1400. A buffer solution is introduced into the inlet orifice 1430b, the buffer and the sample being introduced at respective flow rates capable of generating a laminar flow in the separation channel 1450. An ultrasonic transducer, such as a piezoelectric transducer, attached to the separation channel 1450 is then activated by a control signal, so as to carry out a step of separation of said biological sample by acoustophoresis. This separation makes it possible to promote the concentration of the non-specific particles, present in the sample, in the conveying channel 1470b of said acoustophoresis device. The decomplexified sample is obtained in the outlet orifice 1460a. A second step of separation of said concentrated sample by acoustophoresis is also carried out on the part resulting from the first separation in the channel 1450'. For this, a clean second buffer is simultaneously introduced into the inlet orifice 1430b' in order to extract the residual species of interest still present in the concentrated sample. This separation makes it possible to promote the concentration of the non-specific particles, still present in the concentrated sample, in the outlet orifice 1460c of said acoustophoresis device. The concentrated sample is then decomplexified a second time and then obtained in the outlet orifice 1460b. The collection and the mixing of the decomplexified samples from the outlet orifices 1460a and 1460b make it possible to increase the collection yield of the microorganisms initially present in the biological sample. Indeed, the microorganisms entrained with the non-specific particles during the first separation toward the channel 1450' via the channels 1440a' and 1440c' are capable of being separated by acoustophoresis in this channel 1450' and of thus being capable of being collected following this second separation in the orifice 1460b. The microorganism extraction yield is thus improved.

The relative position and the length of the second separation channel 1450' with respect to the main separation channel 1450' is chosen according to the desired applications, performances and flow rates. Advantageously, two buffer solutions of different type and density are introduced into the inlet orifices 1430b and 1430b'.

Figure 7A:
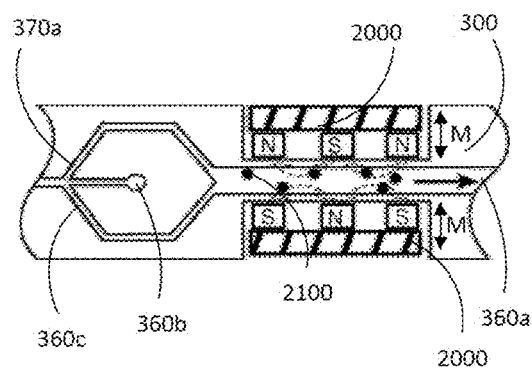
FIG. 7a represents a first alternative of production of the outlet orifices of the devices according to the invention.

Whatever the embodiment of the device according to the invention, the device may comprise, around the conveying channel toward an outlet orifice containing the decomplexified sample, mobile magnet supports which allow the capture of sample placed in the presence of magnetic particles such as magnetic silica. As represented in FIG. 7a, at the outlet of the device 300, two mobile magnet supports 2000 are placed in proximity to the orifice 360a. The magnets thus placed on each side of the conveying channel toward the outlet orifice 360a make it possible to capture microorganisms, in continuous flow, by movement of magnetic silica particles 2100 perpendicularly to the flow of the decomplexified sample. The movement M of the magnet supports is carried out for example perpendicularly to the channel and alternatively between the two supports in order to promote mixing of the sample and of the particles.

Figure 7B:
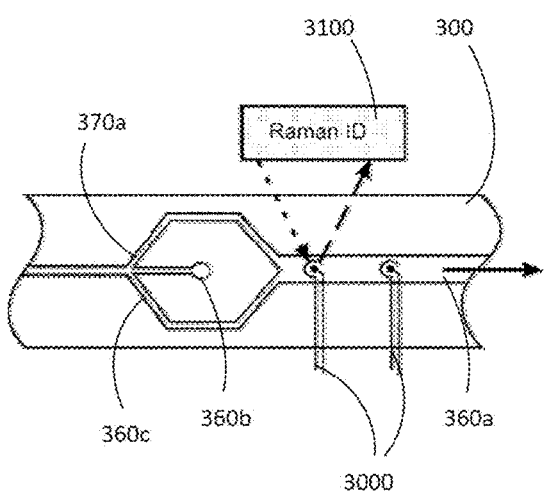
FIG. 7b represents a second alternative of production of the outlet orifices of the devices according to the invention.

Whatever the embodiment of the device according to the invention, the device may comprise, around the conveying channel toward an outlet orifice containing the decomplexified sample, dielectrophoresis (DEP) electrodes deposited on the surface of the device at the level of the outlet orifice. As represented in FIG. 7b, at the outlet of the device 300, two dielectrophoresis (DEP) electrodes 3000 are placed in proximity to the orifice 360a in order to make it possible to carry out a specific capture step. These electrodes can be either functionalized with capture antigens in the case of capture on a panel of desired species, or non-functionalized, then using only the well-known properties of capture by charge of the DEP technique. The identification of the species of interest which is (are) captured can, in the two situations, be confirmed or carried out for example by Raman identification 3100.

Figure 8:
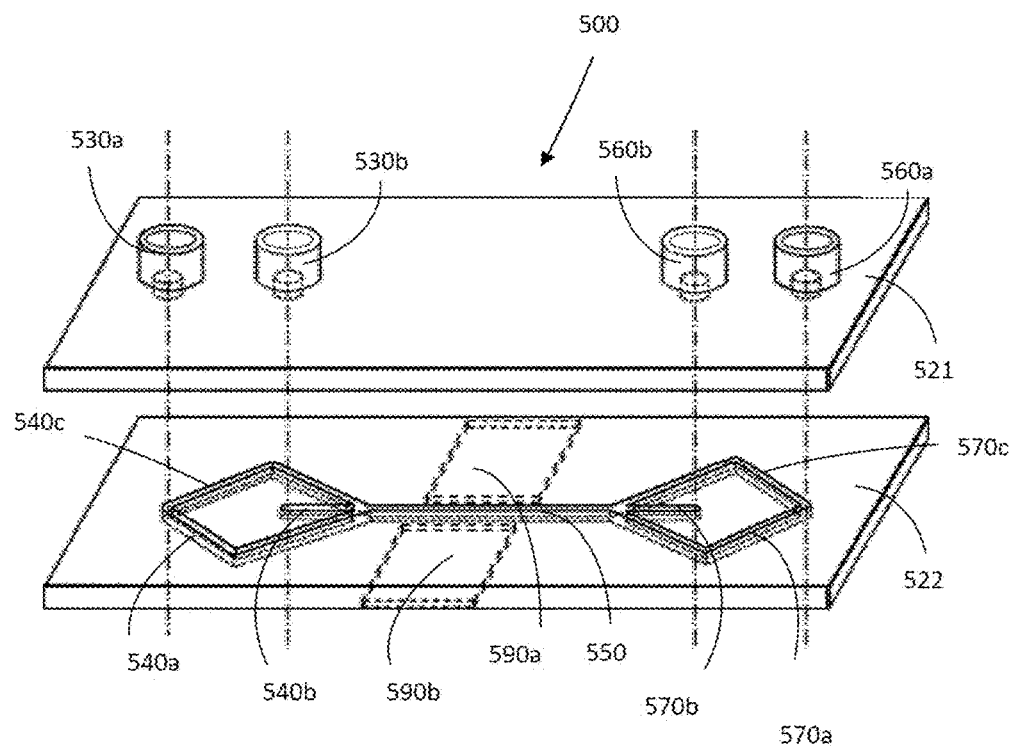
FIG. 8 represents a perspective view of a sixth microfluidic device with two inlet orifices according to the invention, capable of carrying out the process according to the invention.

As represented in FIG. 8, the invention also relates to a sixth device 500 comprising two fluidic parts, a separator 522 and a cover plate 521, these two parts being substantially planar. These two parts are assembled hermetically. Fluidic channels are made in the separator 522. The device 500 comprises two inlet orifices 530a, 530b, made in the cover plate 521, in fluidic communication with at least one separation channel 550 by means of conveying channels respectively 540a, 540c, for the orifice 530a and 540b for the orifice 530b. The separation channel 550 is also in fluidic communication with two outlet orifices 560a, 560b, by means of conveying channels, respectively 570a and 570c for the orifice 560a, 570b for the orifice 560b. The inlet and outlet orifices form reservoirs so as to be able to carry out operations of depositing a sample to be decomplexified by pipetting and the buffer solution and also operations of connecting to a system for pressurizing or placing under vacuum, servo-controlled and regulated on the basis of the flow rate measurement and making it possible to reproducibly control the introduction and the flow of the biological samples and of the buffer in the separation channel. The device 500 is arranged such that an ultrasonic transducer, not represented, can be integrated into or attached to a wall of said separation channel 550. The ultrasonic transducer thus integrated or attached is capable of transmitting mechanical oscillations in multiple acoustic waves that can act on the content of the separation channel and generate therein a standing acoustic wave. An alternating current generator, not represented, can be electrically connected to the transducer in order to generate a transducer control signal of which the frequency, the waveform and the amplitude are known.

In one particular embodiment of the device 500, the separator 522 is made of a glass plate 1 mm thick, coated with a layer of chromium and with a layer of photosensitive resin. After development of the photosensitive layer, the glass is etched with hydrofluoric acid (HF). The conveying channels 540a and 540c, 570a, 570c have a depth P of 125 μm, a lower width Lmin, at the bottom of the channels, of 300 μm, and an upper width Lmax of 550 μm in the plane of the separator in contact with the cover plate. The conveying channels 540b, 570b and also the separation channel 550 have a depth P of 125 μm, a lower width Lmin, at the bottom of the channels, of 375 μm, and an upper width Lmax of 625 μm in the plane of the separator in contact with the cover plate. The cover plate is pierced so as to produce the inlet and outlet orifices and then thermally bonded with the separator in order to produce a sealed assembly. The conveying channels of the inlet orifices (540a, 540b, 540c) have an angle of respectively 45°, 0° and minus 45° relative to the separation channel 550 in the plane of the separator, so as to slow down the flow rate of the fluids originating from the conveying channels having an angle of 45° or −45°, 540a, 540c, relative to the separation channel. The rectilinear separation channel 550 has a length of 80 mm, allowing the cells, particles or molecules to become acoustically concentrated in the conveying channel 570b during operation of the system. The axis of the conveying channel 570b is identical to the axis of the separation channel 550.

Alternatively, the separator 522 of the device 500 comprises two recesses, 590a, 590b, made along the separation channel 550, and capable of each receiving an ultrasonic transducer (which are not represented). This embodiment makes it possible to obtain a standing wave in the separator 522 if the latter is made of a material which does not reflect acoustic waves very much, the material being flexible and thin such as plastic, polymer or silicone materials. A silicone preferentially used is polydimethylsiloxane (PDMS). Preferentially, each ultrasonic transducer comprises a quarter-wave adapter plate of which the acoustic impedance is calculated so as to minimize the energy losses, and thus the heating, between the ultrasonic transducer and the walls of the device.

Preferentially, the cover plate (not represented) is made of PDMS or of molded plastic such as polycarbonate (PC), poly(methyl methacrylate) (PMMA), polypropylene (PP), polystyrene (PS), acrylonitrile butadiene styrene (ABS), cyclic olefin copolymer (COC), cyclic olefin polymer (COP) or polyoxymethylene (POM).

This device 500 is capable of carrying out processes for preparing biological samples by acoustophoresis such as the process according to the invention. For this, all or part of the biological sample to be treated is introduced into the inlet orifice 530a of the device 500. A buffer solution is introduced into the inlet orifice 530b, the buffer and the sample being introduced at respective flow rates capable of generating a laminar flow in the separation channel. An ultrasonic transducer, such as a piezoelectric transducer, attached to the separation channel is then activated by a control signal, so as to carry out a step of separation of said biological sample by acoustophoresis. This separation makes it possible to promote the concentration of the non-specific particles, such as formed elements of the blood, present in the sample, in the outlet orifice 560*b* of said acoustophoresis device. The decomplexified sample is obtained in the outlet orifice 560*a*. The concentrated sample is obtained in the outlet orifice 560*b* (waste zone).

Figure 9:
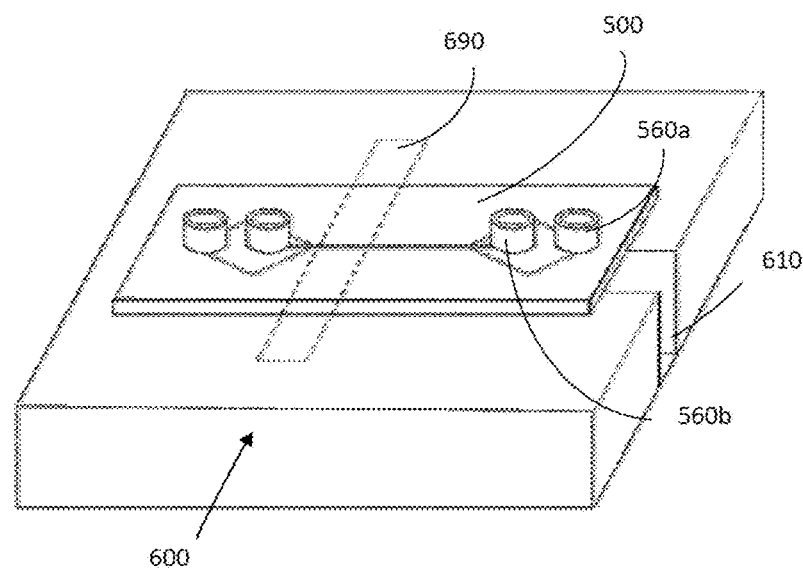
FIG. 9 represents a perspective view of a first support for microfluidic devices according to the invention, capable of carrying out the process according to the invention.

FIG. 9 represents a support 600 for devices with a device 500 placed and held on the support. This support makes it possible, for example, to treat one and the same biological sample simultaneously on several devices or several different samples simultaneously by connecting one or more reservoir(s) containing the sample(s), such as a syringe, to the various inlet orifices of the devices placed on the support. Alternatively, the support may comprise an articulated cap, not represented, which makes it possible to directly connect the inlet and outlet orifices of the device to pressurizing and/or vacuum means, on closing of the cap. This support comprises one or more bases (not represented) for receiving devices according to the invention, making it possible to place and hold said devices. The holding of the devices can be carried out mechanically or by suctioning the devices onto the receiving base(s). Ultrasonic transducers 690 can be placed in these bases so as to be able to create a standing wave in each of the devices placed on the support. The transducer is attached to the device when said device is placed in said base. Alternatively, a single ultrasonic transducer covering several devices can be placed in such a way as to be able to create a standing wave in each of the devices placed on the support.

A receiving space 610 makes it possible in particular to attach a heating system (not represented) to at least one of the outlet orifices of the device placed on the support. Said heating system makes it possible to incubate the biological sample treated and contained in at least one of the outlet orifices 560*a*, 560*b*. Furthermore, the receiving space 610 can comprise a means for measuring the optical density of the sample contained in at least one of the outlet orifices 560*a*, so as to avoid additional handling in order to carry out this operation. Furthermore, the support may be placed directly on a shaker or may comprise a shaking means so as to carry out a step of shaking the biological sample contained in one of the outlet orifices, before, during or following an incubation step.

This support 600 also makes it possible to place and maintain various devices 200, 300, 400, 500, 800, according to the invention, it being possible for the receiving space 610 to be easily adjusted by those skilled in the art.

Figure 10:
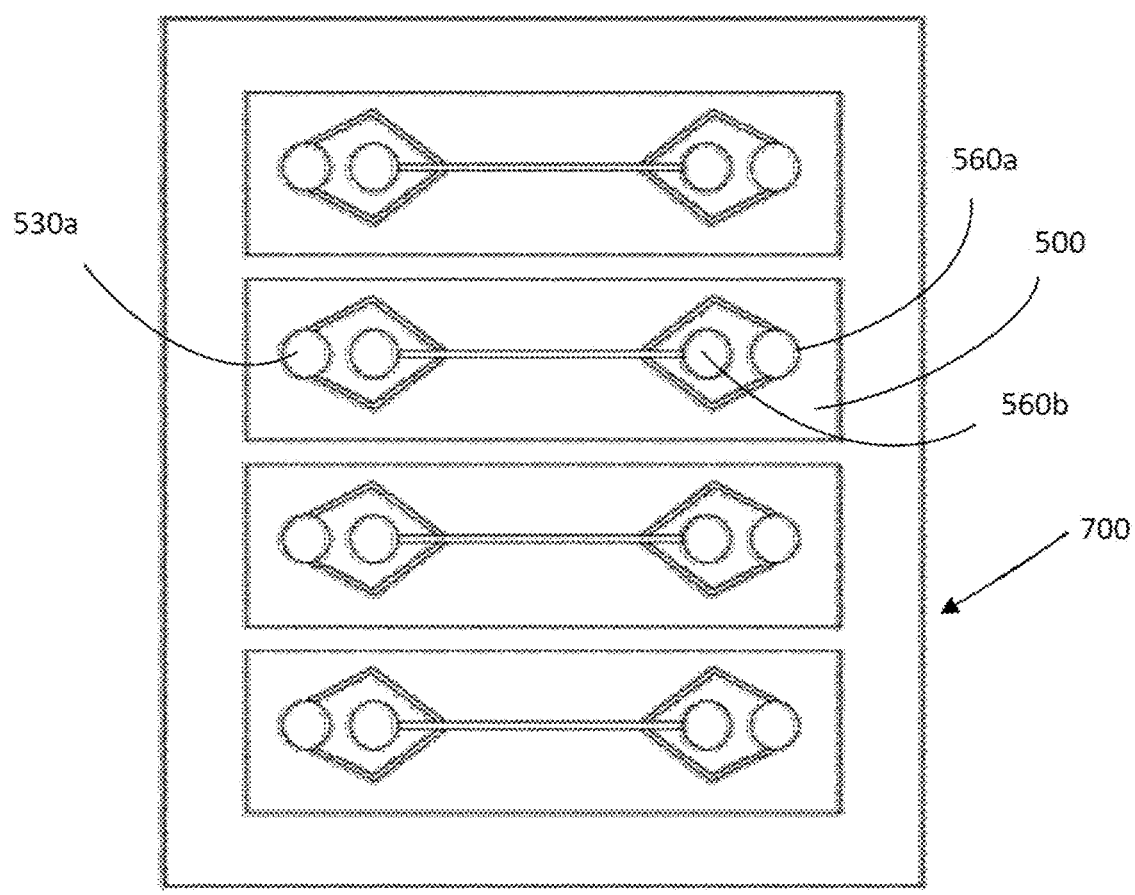
FIG. 10 represents a perspective view of a second support for microfluidic devices according to the invention, capable of carrying out the process according to the invention.

FIG. 10 presents a support 700 for devices according to the invention represented with four devices 500 placed and held on the support. This support makes it possible for example to treat one and the same sample simultaneously on several devices by connecting a reservoir containing the biological sample, such as a syringe, to the various inlet orifices 530*a* of the devices placed on the support. Alternatively, the support makes it possible to place the devices in such a way as to have each of the inlet and outlet orifices aligned on one and the same axis and according to a defined spacing. This spacing can advantageously be equivalent or multiple with respect to that of the pitch of a microplate known to those skilled in the art. In this way, the automatic or manual pipetting operations can be carried out directly in several devices simultaneously, in particular using a pipette or a microplate distributor. This support comprises several bases (not represented) for receiving devices according to the invention, making it possible to place and maintain said devices. Ultrasonic transducers (not represented), or one transducer common to several devices, can be placed in these bases so as to be able to create a standing wave in each of the devices placed on the support. The transducer is attached to the device when said device is placed in said base. In a manner identical to the support 600, the support 700 may comprise several receiving spaces (not represented) making it possible in particular to attach, to at least one of the outlet orifices of each of the devices placed on the support, a heating system (not represented) making it possible to incubate the biological sample treated and contained in at least one of the outlet orifices 560*a*, 560*b*. Furthermore, each of the receiving spaces may comprise a means for measuring the optical density of the sample contained in at least one of the outlet orifices 560*a*, so as to avoid additional handling in order to carry out this operation. Furthermore, the support 700 may be placed directly on a shaker or may comprise a shaking means so as to carry out a step of shaking the biological sample contained in one of the outlet orifices, before, during or following an incubation step. This support 700 also makes it possible to arrange in parallel several of the various devices 200, 300, 400, 500, 800, according to the invention, it being possible for the number of receiving bases to be easily adjusted by those skilled in the art. The various devices placed on the support 700 may be of the same type or of different types.

As represented in FIGS. 11, 12*a* and 12*b*, the invention also relates to a multiplex device 800 comprising three fluid parts, a separator 822, a cover plate 821 and a base 823, these three parts being substantially planar. These three parts are assembled hermetically. Fluidic channels are made in the separator 822. The device 800 comprises two inlet orifices 830*a*, 830*b*, in fluidic communication with eight separation channels 850, by means of a network of introduction channels 841, 842, and of conveying channels. Thus, the separation channels 850 communicate with the orifice 830*a* via the network of introduction channels 841 and also via the conveying channels 840*a*, 840*c*. In the same way, the separation channels 850 communicate with the orifice 830*b* via the network of introduction channels 842 and also via the conveying channel 840*b*. The separation channels 850 are also in fluidic communication with two outlet orifices 860*a*, 860*b*, by means of a network of suctioning channels 843, 844 and of conveying channels. Thus, the separation channels 850 communicate with the orifice 860*a* via the network of suctioning channels 843 and also via the conveying channels 870*a*, 870*c*. In the same way, the separation channels 850 communicate with the orifice 860*b* via the network of suctioning channels 844 and also via the conveying channel 870*b*. Eight separation channels 850 are represented, each of the channels 850 and of the associated suctioning channels forming a fluidic unit repeated eight times.

The device 800 is arranged so that an ultrasonic transducer, not represented, can be integrated into or attached to a wall of said separation channels 850. The ultrasonic transducer thus integrated or attached is capable of transmitting mechanical oscillations in multiple acoustic waves that can act on the content of each separation channel and generate therein a standing acoustic wave. An alternating current generator, not represented, can be electrically connected to the transducer in order to generate a transducer control signal of which the frequency, the waveform and the amplitude are known. Alternatively, through-openings 880 or etchings having a depth greater than or equal to that of the separation channels are made in the separator. These openings or etchings are distributed on each side of the separation channels 850. These openings 880 can be used between the various separation channels and make it possible to obtain better acoustic separation of the resonances of each separation channel.

The networks of introduction channels 841, 842 make it possible to divide the flow, for example of biological sample or buffer introduced into the inlet orifices 830a and 830b. This parallelization of the separation channels makes it possible to treat a volume of sample by acoustophoresis at higher flow rates than on a conventional device, without degrading the extraction performance levels due to the increase in sample flow rate (in µl/min). Thus, if the networks divide the flow of sample introduced in half, conveying the sample to two separation channels, a flow rate that is twice as high can be achieved for one and the same level of decomplexification. In the same way, the suctioning networks 843, 844 make it possible to collect the samples or buffers treated in a single outlet orifice. These networks also make it possible to ensure a pressure equilibrium downstream of the step of separation by acoustophoresis.

This device 800 is capable of carrying out processes for preparing biological samples by acoustophoresis such as the process according to the invention. For this, all or part of the biological sample to be treated is introduced into the inlet orifice 830a of the device 800. A buffer solution is introduced into the inlet orifice 830b, the buffer and the sample being introduced at respective flow rates capable of generating a laminar flow in the separation channels. An ultrasonic transducer, such as a piezoelectric transducer, attached to the separation channels is then activated by a control signal, so as to carry out a step of separation of said biological sample by acoustophoresis. This separation makes it possible to promote the concentration of the non-specific particles, such as formed elements of the blood, present in the sample, in the outlet orifice 860b. The decomplexified sample is obtained in the outlet orifice 860a. The concentrated sample is obtained in the outlet orifice 860a. Since this device has eight separation channels, a biological sample treatment flow rate eight times higher than a prior art device can be achieved on one and the same device. In the same way, a volume of sample (in ml) eight times higher can be treated in an identical time without flow rate modification (µl/min), thus keeping the extraction performance levels intact.

More generally, this fifth multiplex device comprises two inlet orifices in fluidic communication with at least two separation channels, by means of a network of introduction channels and conveying channels. Said separation channels also communicate with two outlet orifices by means of a network of suctioning channels and of conveying channels. This implementation unit associated with each of the separation channels makes it possible to adjust the sample treatment flow rate according to the desired application, by multiplying the number of parallelized separation channels and of associated conveying channels.

Figure 13A:
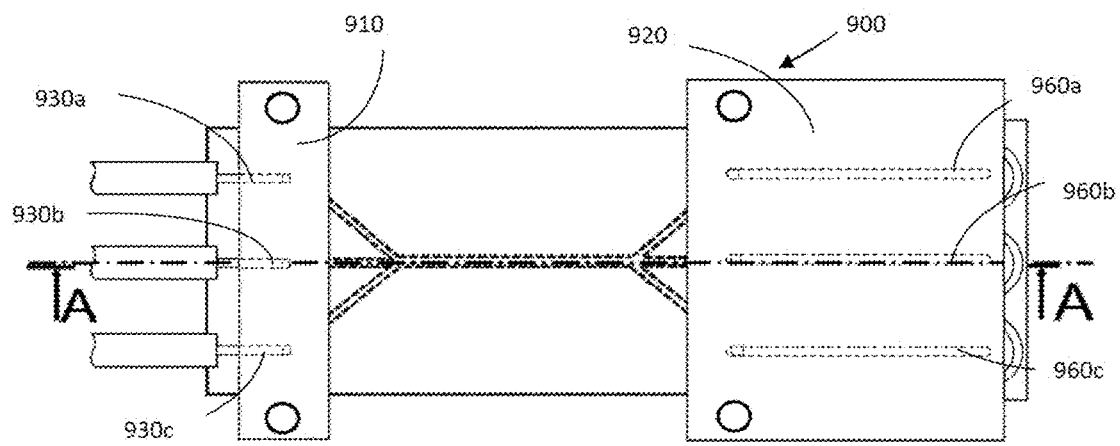
FIG. 13a represents a connection device according to the invention viewed from above.
Figure 13B:
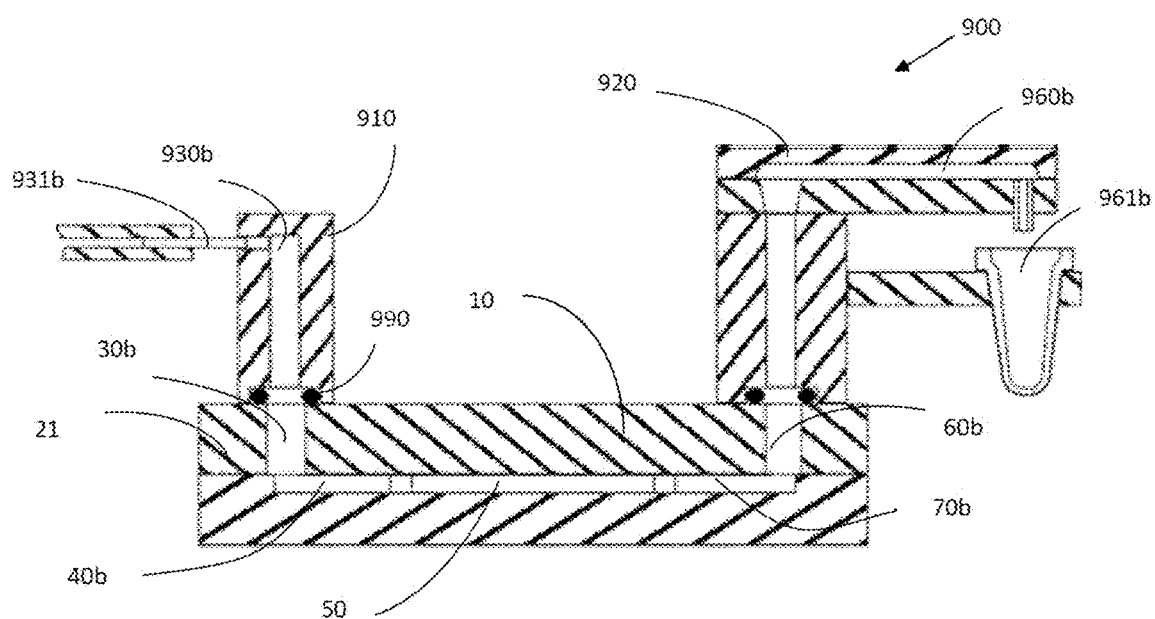
FIG. 13b represents the connection device along the section A-A of FIG. 13a, FIG. 14 represents a diagrammatic view of an air regulation system which allows a method according to the present invention to be carried out and also a connection device according to the invention.

As represented in FIGS. 13a and 13b, the invention also relates to a connecting device 900 which makes it possible to connect orifices of a microfluidic device to an introduction or suctioning means. This device is represented connected to a device 10 of the prior art.

The connecting device 900 comprises an inlet connector 910 and an outlet connector 920. The inlet connector 910 comprises three conveying channels 930a, 930b, 930c capable of cooperating with the inlet orifices of the device 10, respectively 30a, 30b, 30c. The inlet connector 910 thus makes it possible to connect means for introducing biological sample or buffer solution without directly handling the microfluidic device 10. For example, an introduction tube of a syringe 931b, visible in FIG. 13b, is connected to the conveying channel 930b in order to be able to introduce a solution into the orifice 30b. A similar arrangement is carried out facing the inlet orifices 30a and 30c in order to be able to introduce the biological sample into the inlet orifices 30a and 30c.

The outlet connector 920 comprises three conveying channels 960a, 960b, 960c capable of cooperating with the outlet orifices of the device 10, respectively 60a, 60b, 60c. The outlet connector 920 thus makes it possible to connect means for suctioning or means for collecting biological sample or buffer solution without directly handling the microfluidic device 10. For example, a collecting tube 961b visible in FIG. 13b, such as an "Eppendorf" tube, is placed facing the conveying channel 960b in order to be able to collect the solution originating from the outlet orifice 60b. A similar arrangement is carried out facing the outlet orifices 60a and 60c in order to collect the decomplexified sample directly in collecting tubes.

The device 10 is placed between the connectors 910 and 920 and a support, not represented. The connectors 910 and 920 are held on said support by any means, in particular by screwing, by force fitting or by return springs, so as to provide a hermetic connection with the entry and outlet orifices of the device. Advantageously, the connectors comprise O-ring seals 990 in order to guarantee this leaktightness when the connector is held.

Of course, the geometry of this connecting device 900 and of the connectors 910 and 920 and the number of conveying channels of the connectors may easily be adjusted so as to be used with one or more devices 200, 300, 400, 500, 800 according to the invention.

Figure 14:
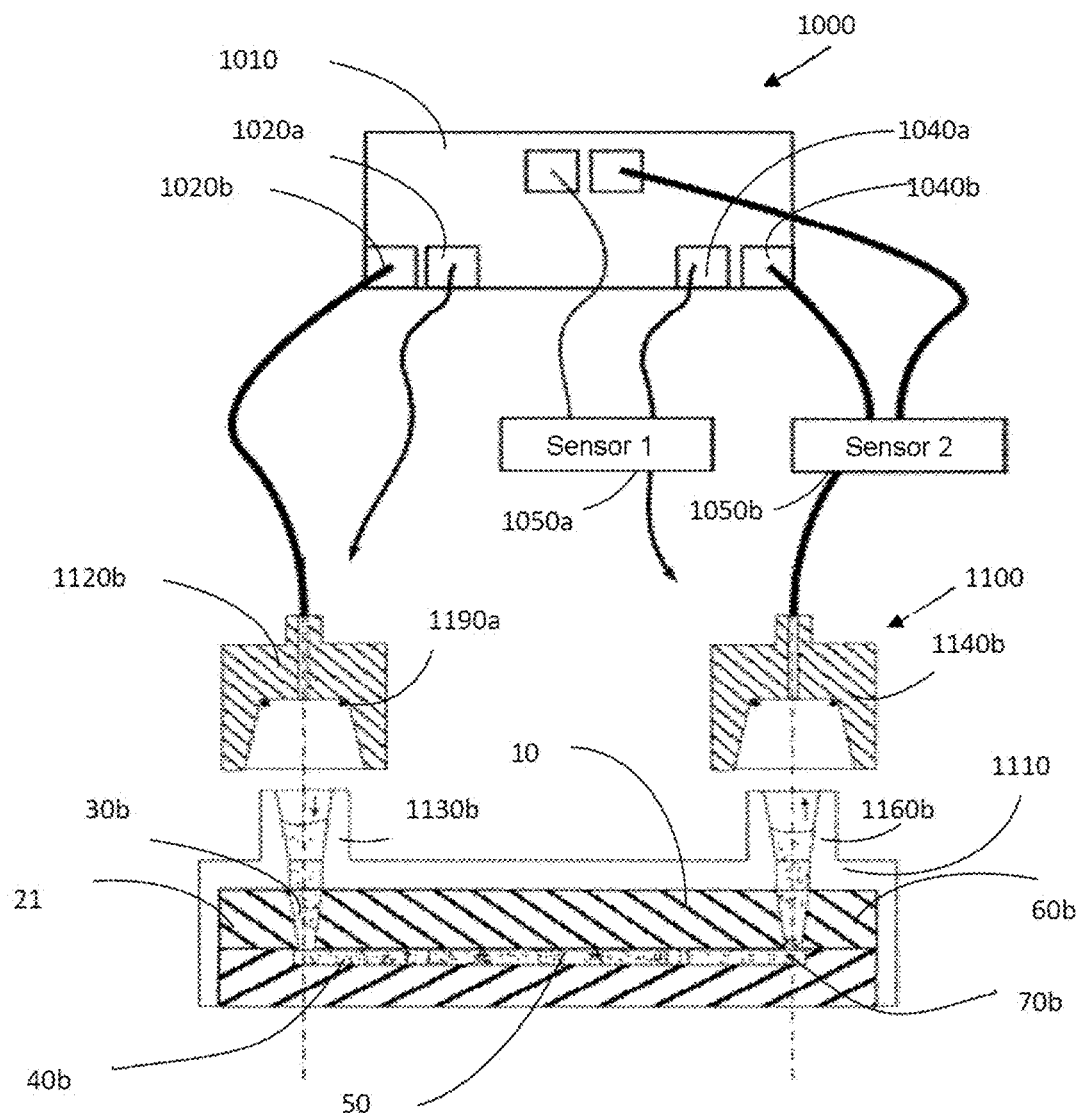

As represented in FIG. 14, the invention also relates to an air regulation system 1000 and associated connecting devices 1100 making it possible to carry out the method according to the invention by servo-control of the introduction and of the suctioning of the liquids introduced. The system is in this case represented with a device 10 of the prior art represented here along section A-A of FIG. 1.

The regulation system 1000 comprises a pressure or vacuum generator 1010. The generator 1010 comprises two pressure outlets 1020a and 1020b capable of delivering the air pressure required for the introduction of the biological sample or of the buffer solution of a method according to the invention at a regulated flow rate in a microfluidic device. The generator 1010 also comprises two vacuum inlets 1040a and 1040b capable of generating an air pressure differential sufficient to suction the biological sample and the buffer solution of a method according to the invention at a regulated flow rate in a microfluidic device. For these purposes, the vacuum inlets 1040a and 1040b are connected to the device via two air flow sensors 1050a and 1050b in order to measure and to servo-control the regulation of air pressure introduced or the vacuum for suctioning of the sample and of the buffer solution of a method according to the invention. This regulation thus makes it possible to obtain a constant flow rate of separation and of decomplexification of the biological sample while limiting the pressure drop risks.

For this purpose, the generator is connected to the two inlet and outlet orifices of the device by means of the connecting device 1100. This device comprises a connector for inlet via inlet orifice and also a connector for outlet via outlet orifice. Only the inlet connectors 1120b and 1140b are represented in the interests of clarity of the figure.

The connecting device 1100 also comprises a cap 1110 placed and held on the device 10. The cap 1110 comprises a reservoir opposite each of the inlet and outlet orifices of the device 10. Only the reservoir 1130b cooperating with the orifice 30b and the reservoir 1160b cooperating with the orifice 60b are represented in the interests of clarity of the figure. The cap 10 can be made of plastic, for example by injection-molding, and makes it possible to cap a device in order to present reservoirs opposite each inlet and outlet orifice of the device held. These reservoirs can in particular be used for depositing and collecting samples and buffer solutions. The cap is held on a support, not represented, in such a way as to make a hermetic connection with the orifices of the device 10. The cap can be held on the support by any means, in particular by screwing, by force fitting or by the pressure of a return spring.

An inlet connector 1120b is capable of being placed and held on the cap 1110 so as to cooperate with the reservoir 1130b of said cap. An outlet connector 1140b is also capable of being placed and held on the cap 1110 so as to cooperate with the reservoir 1160b of said cap. The connectors advantageously have O-ring seals for leaktightness and are held on the cap by screws or springs. The connectors can be held on the cap by any means, in particular by screwing, by force fitting or by the pressure of a return spring.

Of course, the geometry of this connecting device 1100 and in particular of the connectors may be easily adjusted so as to be used with a device 200, 300, 400, 500, 800 according to the invention.

The examples hereinafter will make it possible to understand the present invention more clearly. However, these examples are given only by way of illustration and should in no way be regarded as limiting the scope of said invention in any way.

Example: Treatment of Blood Samples According to the Method

A) Assembly of a Device and of a System for Carrying Out the Method According to the Invention A microfluidic device is produced in accordance with the device represented in FIG. 1.

Figure 3:
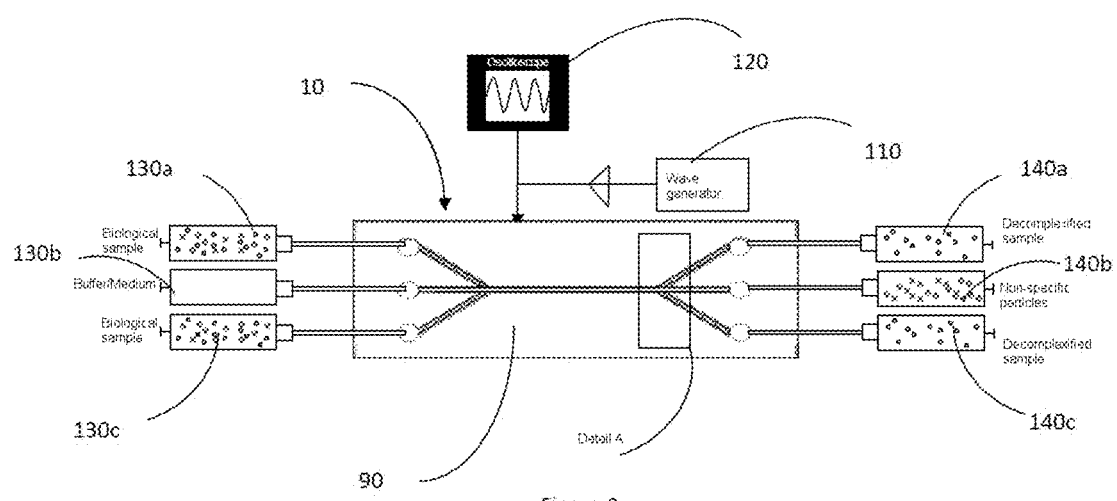
FIG. 3 represents a diagrammatic view of a system for carrying out a method according to the present invention using a microfluidic device according to the prior art.

As illustrated in FIG. 3, the three inlet orifices 30a, 30b, 30c, and the three outlet orifices 60a, 60b, 60c, are connected to introduction means, such as syringes (Becton Dickinson Plastipak™, Spain) via an assembly comprising a pipette tip (Eppendorf, United Kingdom) connected to a Tygon tube (ID 0.03, OD 0.09 Cole-Parmer, United Kingdom). A pipette tip is hermetically bonded to each of the orifices, a Tygon tube is then inserted into and then bonded in the pipette tip and, finally, assembled with the syringe end piece. In this way, three introduction syringes 130a, 130b, 130c make it possible to introduce a fluid into each of the inlet orifices 30a, 30b, 30c, while three suctioning means such as syringes 140a, 140b, 140c make it possible to suction the fluid in each of the outlet orifices 60a, 60b, 60c. Alternatively, a connecting device 900 can be used to connect each syringe to the device.

The three suctioning syringes 140a, 140b, 140c make it possible to ensure a pressure equilibrium, and a flow rate equilibrium, in the three conveying channels to the outlet orifices, downstream of the separation channel. In this way, the device is less subject to possible blockages that can be due to large particles hindering the circulation of the fluid in one of the channels.

Syringe pumps (Harvard Apparatus, United Kingdom), not represented, are used to control the sample and buffer introduction flow rates.

A piezoelectric transducer with dimensions of 10 mm×30 mm, made of ceramic (Pz26, Ferroperm Piezoceramics, USA), with a resonance frequency range of 1 MHz to 2 MHz is attached to the device 10 by an ultrasound gel (Anagel™ United Kingdom). This transducer makes it possible to generate ultrasound used to induce a standing wave between the walls of the separation channel. Motion of the particles induced by the acoustophoresis phenomenon can thus be obtained by applying an alternating current (AC) to the transducer. This control signal is introduced into the circuit by a function generator (Agilent, model 33210A, 10 MHz on the function/generator of arbitrary waveform, United Kingdom) in sinusoidal operating mode. An amplifier (Amplifier research, model 1W1000B, 1-1000 MHz, AR) is used to amplify the signal originating from the function generator and to obtain the required amplitude for entraining the particles. An oscilloscope (Tektronix, model 1042 SCT, USA) is connected in parallel with the sensor in order to measure the operating voltage.

B) Preparation of Inoculated Blood Samples

In order to avoid problems of blocking of the microfluidic device used, defibrillated horse blood was used. 9 ml of horse blood (Oxoid, ThermoScientific, UK) were defibrillated by means of a Porex filter (porosity of 25 μm) and then mixed with 1 ml of trisodium citrate at 3.3% w/v.

In order to prepare an inoculated sample containing a controlled inoculum of pathogenic organisms, an isolated colony of *Salmonella typhimurium* (NCTC 12023/ATCC® 14028, Pro-lab Diagnostics, UK) isolated from a culture on Trypticase Soy Agar culture medium (TSA; bioMérieux, France) is diluted in 9 ml of Trypticase Soy Broth (TSB; bioMérieux, France) then incubated at 37° C. for 18 h.

Approximately 0.4 ml of enriched both thus obtained is diluted in 9 ml of BPW and its absorbance at 600 nm is measured (CECIL 1011 apparatus, series 1000) so as to obtain a reading of 0.100 corresponding to approximately $1.0 \times 10^9$ CFU·ml$^{-1}$. From this enriched broth, 6 series of dilutions are then prepared and number from d-1 to d-6 corresponding to concentrations of $10^8$ to $10^3$ CFU·ml$^{-1}$ (CFU meaning colony forming units).

In order to determine the amount of pathogens present in the batches of sample containing a controlled inoculum thus obtained, a TSA culture medium (controlled inocula; TSA× 2) is inoculated with 100 μl of d-6 and incubated at 37° C. overnight. This step is carried out in duplicate. The actual number of microorganisms present in the initial sample was calculated according to the dilution and the number of colonies counted on the medium.

0.1 ml of $10^9$ CFU·ml$^{-1}$ of *Salmonella typhimurium* is subsequent inoculated into the blood mixture, prepared as indicated above, so as to obtain a final concentration of *Salmonella typhimurium* of $10^7$ CFU·ml$^{-1}$. The blood mixture inoculated with $10^7$ CFU·ml$^{-1}$ of *Salmonella typhimurium* was then diluted with a phosphate buffered saline (PBS) solution (1:1 ratio by volume) and used for the following examples.

This preparation is equivalent to a conventional concentration of microorganisms in the case of a positive blood culture.

C) Step of Decomplexification by Acoustophoresis

The recovery of the blood cells after their treatment in a microfluidic device by means of a process according to the invention was determined using a hemocytometer. The suspension collected from each outlet orifice was diluted with a PBS solution until the number of cells counted on the basis of each square of a counting cell (of Thoma or Malasse type)

was between 50 and 100. The rejection rate of the blood cells in the outlet orifice placed in the axis of the separation channel is calculated by:

$$\text{Rejection rate } (\%) = 100 \times \frac{\text{(number of blood cells in the outlet orifice in question)}}{\text{(total number of blood cells in all the outlet orifices)}}$$

Other indicators are:
The quality of the extraction, which will be given by the composition of each outlet of the device (flow cytometry analysis method).
The extraction yield, which represents the percentage of bacteria separated relative to the concentration of the starting sample (method of analysis by plating out on dishes and counting).
The bacterial growth indicates whether the acoustic sorting makes it possible to preserve the viability of the microorganisms without imposing too great a stress on them (method of analysis: measurement of optical density of the decomplexified sample after extraction and after incubation at 37° C.).

The inoculated blood mixture at $10^7$ CFU·ml$^{-1}$ of *Salmonella typhimurium* is diluted in PBS in a ratio of 1:1, prepared according to the description above and filtered by means of a Porex filter and then introduced into the inlet orifices 30a and 30c of a device 10 of the prior art, as described previously and represented in FIG. 1. The inlet orifices 30a and 30c are also called side inlets. The device 10 is connected to introduction syringes 130a, 130b, 130c, and suctioning syringes 140a, 140b, 140c, as described previously and according to FIG. 3. An ultrasonic transducer 90 is attached to the separation channel 50. A wave generator 110 makes it possible to transmit a control signal to the ultrasonic transducer 90, in this case a piezoelectric transducer. A phosphate buffered saline (PBS) is introduced into the inlet orifice 30b, also called central inlet. The filtration step makes it possible to limit the presence of particles that may block or obstruct the channels of the device and disrupt the laminar flow of the fluids in the separation channel.

The blood sample is introduced into the side inlets at a flow rate of 10 μl·min$^{-1}$. The phosphate buffered saline (PBS) is introduced into the central inlet at a flow rate of 70 μl·min$^{-1}$. A suctioning flow rate of 30 μl·min$^{-1}$ is provided by the suctioning syringes in the outlet orifices 60a, 60b, 60c.

Figure 15A:
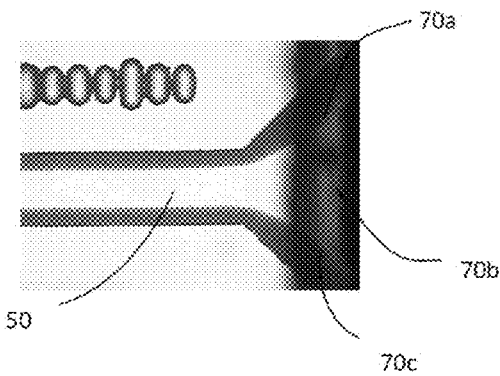
FIGS. 15a and 15b are photographs viewed from above of a part of the microfluidic device of the system according to detail A of FIG. 3, during the method according to the invention.

In the case where no control signal is transmitted to the ultrasonic transducer 90, the flow is laminar all along the separation channel and all the particles of the sample introduced into the inlet orifice 30a move completely toward the outlet orifice 60a. Likewise, all the particles of the sample introduced into the inlet orifice 30c move completely toward the outlet orifice 60c. This flow is carried out for a period of 40 min. Thus, through the experiment, a very small amount of blood cells is observed in the outlet orifice 60b. This flow is visible in FIG. 15a, the blood cells being darker on the image and concentrated only in the conveying channels 70a and 70c, to the outlet orifices, respectively 60a and 60c.

Figure 15B:
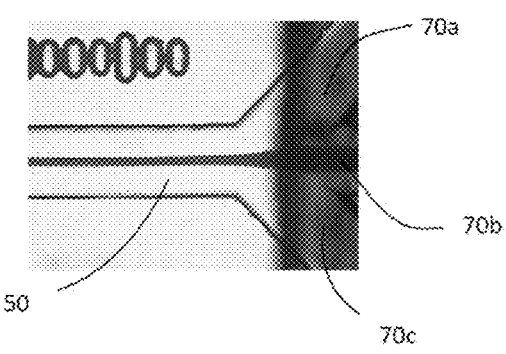

In a second step, the experiment is repeated according to the same protocol, while applying a control signal having a frequency of 1300 MHz, and having an amplitude of 36.6 V peak-to-peak (Vp-p), to the piezoelectric transducer. The flow is then laminar at the entry of the separation channel and then migration of the blood cells to the center of the separation channel is observed. Thus, all the blood cells of the sample introduced into the inlet orifices 30a and 30c move toward the outlet orifice 60b. This flow is carried out for a period of 40 min. This flow is visible in FIG. 15b, the blood cells being darker on the image and concentrated only in the conveying channel 70b to the outlet orifice 60b. Only a mixture of PBS buffer and plasma, which may contain the microorganisms present in the sample introduced into the device, remains in the conveying channels 70a and 70c.

This experiment is carried out twice and makes it possible to demonstrate a rejection rate of 99.82% of blood cells in the outlet orifice 60b (% of coefficient of variation=0.043). This experiment demonstrates the capacity of the process according to the invention to efficiently separate blood cells from plasma at a constant flow rate.

Figure 16A:
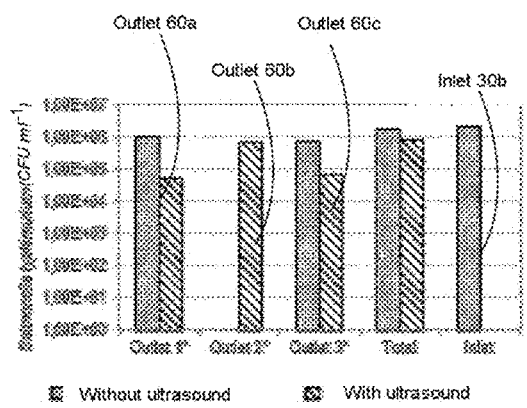
FIGS. 16a and 16b illustrate the results of *Salmonella* counting operations following the treatment method according to the invention.
Figure 16B:
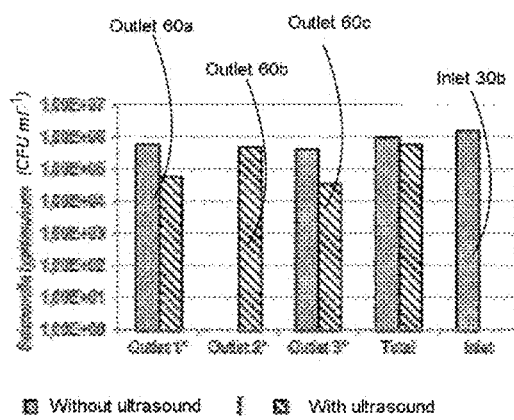

D) Recovery of Microorganisms Present in the Blood Sample 5 ml of the blood sample inoculated at $10^7$ CFU·ml$^{-1}$ are diluted with PBS (1:1 ratio by volume). The protocol described in part C is reproduced and counting is carried out on the samples collected in the outlet orifices (with and without ultrasound). This counting is carried out by inoculation of chromID®—*Salmonella* media (bioMérieux, France) in order to estimate the number of viable colonies after the preparation of the sample according to the process of the invention. The results of these counts are illustrated in FIGS. 16a and 16b. A lower order of magnitude of recovery of the pathogenic agent is observed on the outlets 60a and 60c because of the acoustophoresis. Indeed, the sizes of the *Salmonella typhimurium* cells (diameter: 0.7-1.5 μm and length: 2-5 μm) and the size of the red blood cells (approximately 7 μm) mean that they are both capable of being concentrated by acoustophoresis in the central channel, toward the outlet orifice 60b.

However, this experiment makes it possible to obtain, by virtue of the process according to the invention, a strong decomplexification of the sample, 99.8% of blood cells, and in particular of red blood cells, being rejected, while at the same time guaranteeing a level of pathogens that are viable and sufficiently concentrated to be detectable by conventional techniques. This decomplexification also enables an easier analysis of the samples collected in the outlet orifices 60a and 60c, in particular by online flow cytometry, directly at the outlet of the acoustophoresis device.

E) Separation of Fluorescent Beads by Acoustophoresis

A first solution containing beads of 1 μm (reference 17154, Polysciences) at a concentration of $4.55 \times 10^{10}$ beads/ml is diluted 1000-fold. A second solution containing beads of 10 μm (reference 18140, Polysciences) at a concentration of $4.55 \times 10^7$ beads/ml is diluted 50-fold.

A mixture of beads is obtained by 1:1 mixing of these diluted solutions in order to obtain final concentrations in the solution of $5 \times 10^7$ beads of 1 μm/ml and $1 \times 10^6$ beads of 10 μm/ml.

The mixture of beads of 1 and 10 μm is injected into the side inlets 30a and 30c of a device 10 of the prior art, and water (Suspension Medium bioMérieux) is introduced into the central orifice 30b. The device is used in a system as described in point A.

The samples present in the outlets 60a and 60c are mixed and analyzed using a cytometer. For this, water (Suspension Medium, bioMérieux) is introduced into the central channel of a flow cytometry device (Partec), the cytometer analysis flow rate is adjusted to 1 μl/min and the acquisition is carried out over the course of 60 s.

In order to regulate the cytometer so as to allow the analysis of the mixtures of beads: the bead samples are diluted 100-fold before analysis. The trigger is regulated on the signal FL1, so as to detect only the fluorescent elements (and thus to be able to distinguish the beads of 1 µm from the background noise). The cytometer is thus regulated according to the parameters of the following table 1.

TABLE 1

| Values of the PMT gains for the bead analysis on the cytometer | |
|---|---|
| FSC | 100 |
| SSC | 180 |
| FL1 | 225 |
| FL2 | 350 |

Figure 17:
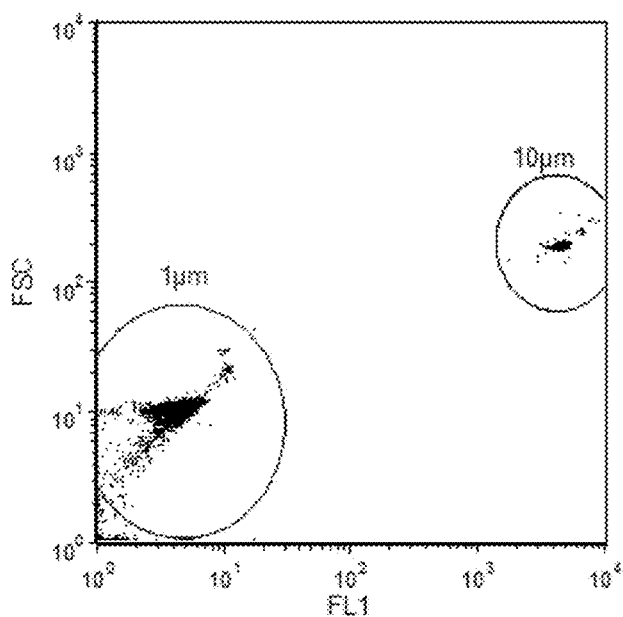
FIG. 17 illustrates the capacity of a cytometer to distinguish beads of 1 μm and of 10 μm.

Two regions can thus be delimited on the FL1-FSC representations in order to distinguish the 1 and 10 µm beads (see FIG. 17).

The number of elements detected in each of these regions can then be exported in order to determine the composition of the sample. This method also makes it possible to verify and set up the parameters of the acoustophoresis system without involving biological samples.

Figure 18:
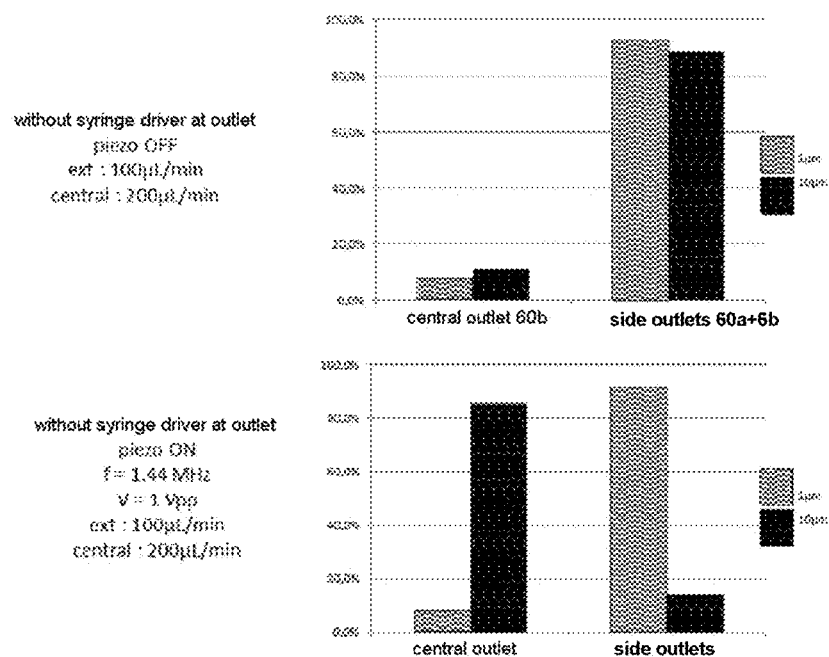
FIG. 18 illustrates the recovery rate of fluorescent beads of 1 μm and of 10 μm following the treatment method according to the invention.

FIG. 18 thus illustrates the possibility of separating the beads of 1 and 10 µm using acoustic forces. When the piezoelectric transducer is not activated, close to 90% of the 1 and 10 µm beads are recovered in the side outlets 60a and 60c of the device, whereas, when it is supplied with a sinusoidal signal of amplitude 1 V peak-to-peak (Vpp) (corresponding to 34 V after amplification) and of frequency 1.44 MHz, the acoustic waves transmitted in the channel allow separation of the 1 and 10 µm beads: approximately 85% of the beads of 10 µm are recovered in the central outlet 60b, whereas 90% of the 1 µm beads are recovered in the side outlets 60a and 60c.

This example makes it possible to validate the capacity of the method to decomplexify fluorescent particles of sizes similar to microorganisms and blood cells and to analyze them by flow cytometry.

F) Treatment of Inoculated Blood Cultures by the Method According to the Invention Three BacT/ALERT® blood culture bottles (bioMérieux, France) having been declared as positive by the BacT/ALERT® instrument (bioMérieux, France) are used. Each of these bottles contains a species of microorganism, namely *Citrobacter freundii* (this bottle was stored for 14 days at 4° C.), *Escherichia coli* and *Enterococcus faecalis*.

The concentration of microorganisms present in these blood cultures is approximately $10^9$ CFU/ml.

The blood culture inoculated is injected at 40 µl/min into the side inlets 30a and 30c of a device 10 of the prior art, as described in point A. Buffer (Suspension Medium 0.85%, bioMérieux) is injected at 100 µl/min into the central inlet 30b. The device is placed on a system as described in point A.

Figure 19A:
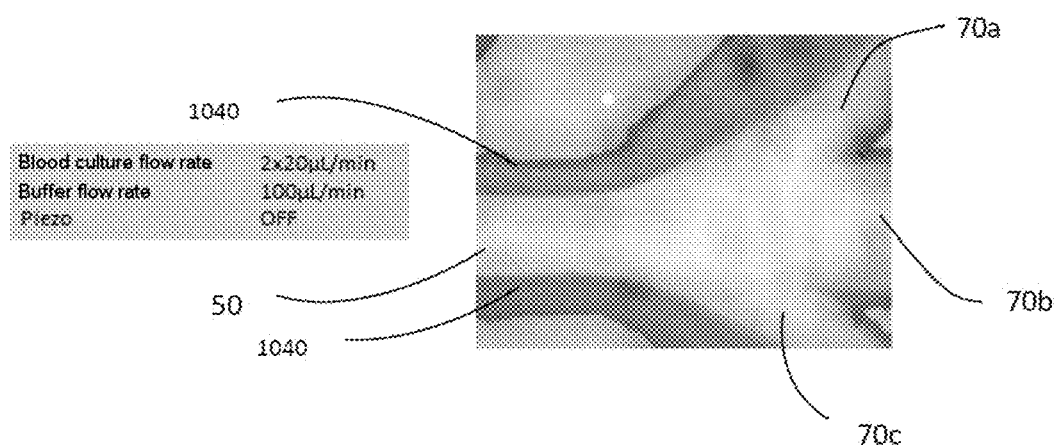
FIGS. 19a and 19b illustrate the effect of the acoustic waves on the focusing of the red blood cells of a blood culture during the treatment method according to the invention.
Figure 19B:
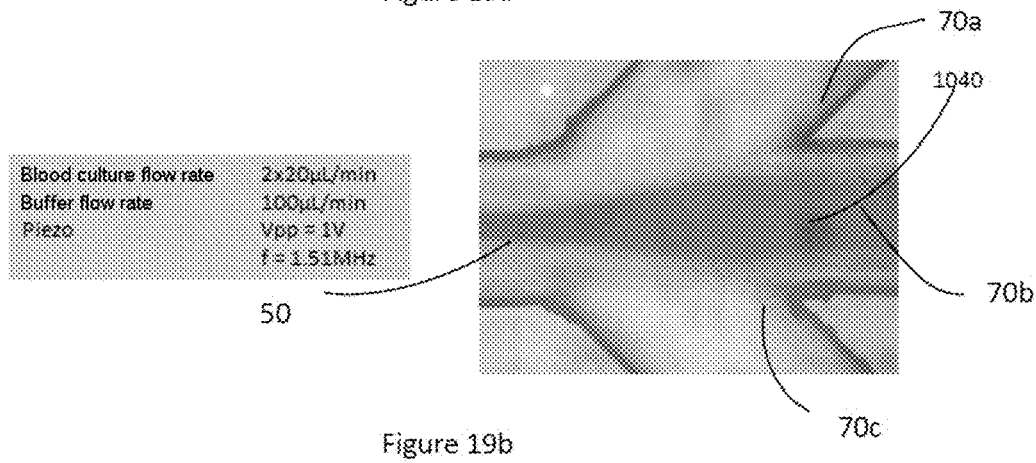

FIG. 19a (without excitation of the transducer) and 19b (with excitation) illustrate the effect of the acoustic waves on the focusing of red blood cells at the center of the channel when the piezoelectric transducer is actuated and at the abovementioned flow rates. This illustrates the possibility of decomplexifying the sample by removing a large part of the formed elements of the blood present in the blood culture.

Figure 20A:
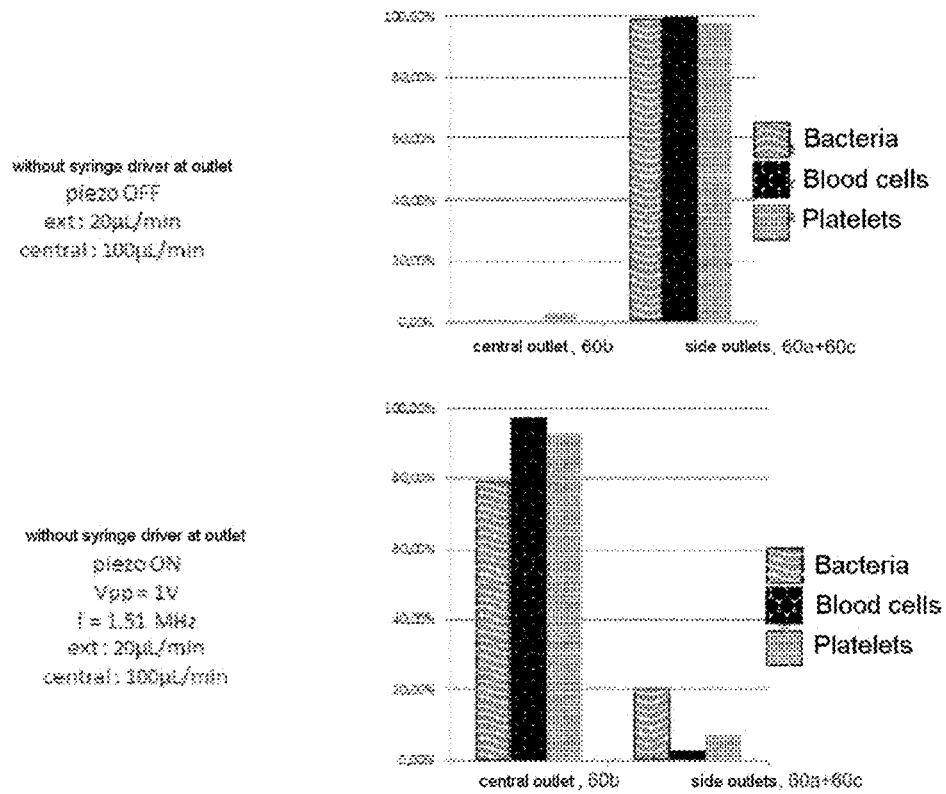
FIG. 20a illustrates the blood cell rejection rate, the blood culture sample being introduced without prior dilution at a flow rate of 20 μl/min.

FIG. 20a illustrates that, under the effect of the acoustic forces (this step is carried out at an excitation frequency of 1.51 MHz), it is possible to reject close to 95% of the blood cells. Nevertheless, only 20% (36% on the replicate) of the bacteria are recovered in the side outlets 60a and 60c. This is because the bacteria, although they have a smaller volume than the blood cells, are also subject to the effects of the acoustic forces and also the effect of entrainment of the red blood cells and concentrate in part at the center of the channel.

Figure 20B:
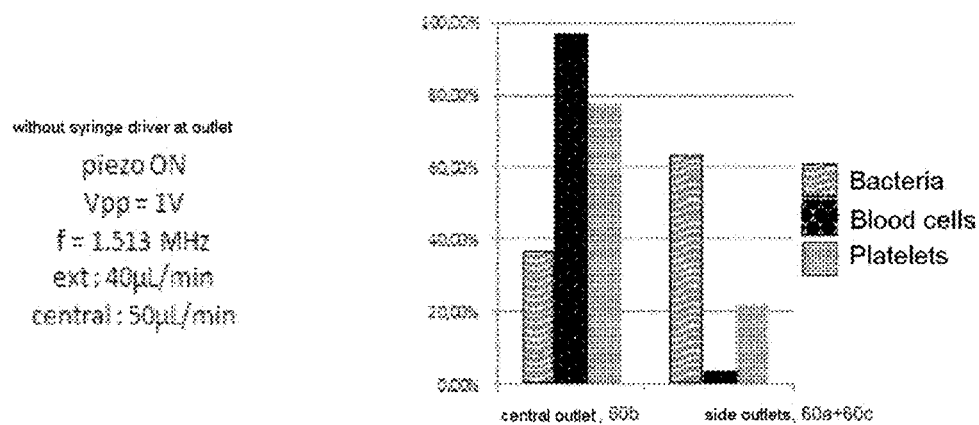
FIG. 20b illustrates the blood cell rejection rate, the blood culture sample being introduced without prior dilution at a flow rate of 40 μl/min.

As illustrated in FIG. 20b, by increasing the flow rate of the samples at inlet (going from 2×20 µl/min to 2×40 µl/min), this focusing of the bacteria is limited, and more than 60% of the bacteria are recovered in the side channels.

In order to analyze the blood cultures by flow cytometry, said cultures are diluted $10^3$-fold in PBS (phosphate buffered saline).

The cytometer is regulated according to the parameters of the following table 2.

TABLE 2

| Values of the PMT gains for the analysis of the blood cultures on a cytometer | |
|---|---|
| FSC | 150 |
| SSC | 257 |
| FL1 | 490 |
| FL2 | 490 |

The samples present in the outlets 60a and 60c are mixed and then analyzed using a cytometer. For this, water (Suspension Medium, bioMérieux) is introduced into the central channel of a flow cytometry device (Partec), the cytometer analysis flow rate is adjusted to 1 µl/min and the acquisition is carried out over the course of 60 s.

Figure 21:
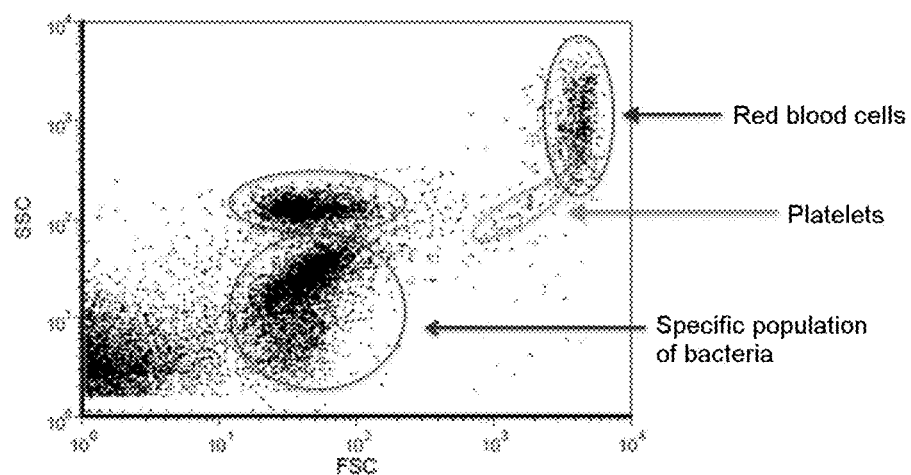
FIG. 21 illustrates the result of the flow cytometry analysis (scattergram) of a sample decomplexified by the treatment method according to the invention.

The result of this analysis by the cytometer makes it possible to observe regions that can thus be delimited in order to distinguish the various components of the inoculated blood cultures (FIG. 21). The number of elements detected in each of these regions can then be exported in order to determine the composition of the sample. Markers specific for red blood cells and for platelets, coupled to fluorophores detectable on FL1 and FL2, can thus be used to obtain a better distinction between the formed elements of the blood and the microorganisms.

This example thus shows that the bacteria are viable after acoustic separation, and that the blood culture can be treated without dilution without any major coagulation problem in the device or the fluidic connections.

The sample flow rates located between 10 and 40 µl/min per inlet for the blood culture and for 1 V peak-to-peak (Vpp), that is to say 34 V peak-to-peak (Vpp) after amplification, for the piezoelectric transducer make it possible to preserve good focusing of the red blood cells in the channel.

It is also noted that, at each extraction test, the frequency is slightly adjusted (+/−50 kHz approximately around a resonance at 1.44 MHz), in order to optimize the focusing of the red blood cells in the separation channel.

G) Treatment of Inoculated Blood Cultures

Whole blood vials (10 ml) are obtained from the French blood bank. In the case of a negative blood culture (i.e. without artificial contamination), the blood is introduced into a bacT/Alert 40 ml BTA bottle (bioMérieux, reference 259789) and then incubated for 24 h at 35.5° C. (homogenization on a roller mixer).

In the case of a positive blood culture, 400 µl of suspension of the microorganism of interest (suspension in tryptone salt), calibrated at $10^3$ CFU/ml, are added in addition to the blood. The bottle is then incubated at 35.5° C. for 18 h with homogenization on the roller for a bacterial culture. For a yeast culture, the bottle is incubated at 30° C. for 36 h with homogenization on a roller. This makes it possible to obtain a microorganism concentration equivalent to that of a positive blood culture bottle.

The three models of microorganisms studied are the following:

E. coli ATCC 25922 (Gram-negative)
S. aureus ATCC 29213 (Gram-positive)
C. albicans ATCC 18804 (yeast).

Two syringe drivers (Pump Elite 11, Harvard Apparatus) are used independently to regulate the inlet flow rates of a device 10 of the prior art (one syringe driver for the side channels 30a and 30c and one syringe driver for the central pathway 30b). The blood culture is loaded into two 5 ml plastic Becton Dickinson syringes put in place on the first syringe driver and the extractor buffer is loaded into a 25 ml plastic Becton Dickinson syringe in the second syringe driver. The sample is treated using a buffer, introduced into the central channel, of 0.85% NaCl physiological saline (bioMérieux) density-adjusted with 1% v/v of Percoll® (Sigma). This isotonic and biocompatible medium guarantees the viability of the cells focused at the center of the channel during the step of separation by acoustophoresis. This buffer is injected into the central inlet 30b. In the case where isotonicity is not desired, the treatment buffer can be replaced with suspension medium (bioMérieux).

The feed can also be carried out by means of a pressure controller (Elvesys); the feed of the channels 30a and 30c is then divided into two, such that it is controlled only by a single pressure standard.

The treatment of the sample, also called extraction, by acoustophoresis is carried out according to the following protocol:

1) Wetting all of the fluidic system with the buffer and sample solutions, at high flow rate (2 ml/min—1 ml sample, 1 ml buffer). This step aims, inter alia, to discharge any air bubbles present in the system.

2) Reducing the flow rate to the optimum point (60 µl/min for the sample, 70 µl/min for the buffer) and supplying the piezoelectric transducer. This step aims to obtain optimal acoustic focusing while assessing, for example visually, the concentration of red blood cells in the central outlet.

3) By maintaining the supply to the actuator, increasing the buffer flow rate (around 2 ml/min) so as to clean the three outlets before treatment/extraction.

4) Reducing the buffer flow rate to 70 µl/min when the three outlets produce a transparent solution.

The extraction begins when the central outlet visually produces a dense red solution.

Counting of the Species in Solution:

Three types of cells are to be counted: the microorganisms, the red blood cells and the platelets.

The microorganisms are counted by plating out on COS or SDA10 nutritive agar (bioMérieux). The solution undergoes a succession of dilutions in suspension medium, resulting in a concentration of a few $10^3$ CFU/ml. 50 µL are then deposited on the agar, plated out and left to incubate overnight. The colonies are then counted by hand or automatically.

The blood cells are for their part counted by flow cytometry (Cyflow, Partec). Their precise identification is provided by the addition of specific markers "human CD41a-PerCP-Vio700" for the red blood cells (Miltenyi Biotec) and "human CD235a-FITC" for the platelets (Miltenyi Biotec). Other than for any exception, 10 µl of each marker are brought into contact with 80 µl of sample and left in the dark for 15 min before being passed through the cytometer.

The microorganism counting step can also be carried out using a cytometer. Computer post-treatment (FCS express) then makes it possible to identify and at the same time to count the three populations of interest by means of exclusion and inclusion gates on the fluorescence channels.

Finally, the microorganisms can be counted by measuring the optical density of the sample ($\lambda=640$ nm) manually (Densimat—bioMérieux) or automatically (Tecan reader—Tecan Group Ltd). These counts make it possible, in the case of acoustophoresis, to quantify three distinguishing parameters.

| Efficiency | Yield | Purity |
|---|---|---|
| $\dfrac{n_{CFU,peripheral}}{n_{CFU,central}+n_{CFU,peripheral}}$ | $\dfrac{n_{CFU,peripheral}}{n_{CFU,source}+n_{CFU,peripheral}}$ | $\dfrac{n_{CFU}}{n_{blood\ cells}+n_{CFU,peripheral}}$ |

The term "nCFU,peripheral" is intended to mean the total number of CFUs (colony forming units) counted using the side outlets of the acoustophoresis device. The term "nCFU, central" is intended to mean the total number of CFUs (colony forming units) counted using the central outlet(s) of the acoustophoresis device. One of the criteria for comparison between the various extraction methods is the return to growth of the microorganisms post-treatment. The latter are placed in suspension in the blood culture medium (the various solutions are calibrated in terms of optical density so as to start from equal starting concentrations), then diluted five-fold in BHI medium (bioMérieux) before being incubated with orbital shaking (300 rpm) at 35.5° C. for the bacteria, 30° C. for the yeasts. The count is carried out hour by hour by flow cytometry.

The post-acoustophoresis identification is carried out by mass spectrometry (Vitek MS—bioMérieux). Briefly, four types of deposits are carried out: crude concentrated sample, centrifuged (14000 rpm/10 min) concentrated sample, concentrated sample centrifuged (14000 rpm/10 min) and resuspended in distilled water, centrifuged (14000 rpm/10 min) resuspension.

For the liquid phases, 1 µL is deposited on a MALDI target, followed by 1 µL of HCCA matrix (bioMérieux). For the solid phases, the centrifugation pellet is removed using a 0.1-10 µL pipette tip and spread on target, followed by 1 µL of matrix. In the case of yeasts, 0.5 µL of formic acid at 10% is deposited before the addition of HCCA matrix. Once prepared, the plate is introduced into a Vitek MS apparatus (bioMérieux) which gives the result of identification or non-identification of each spot.

For this test, only E. coli is studied. Results of identification by mass spectrometry are in particular obtained on E. coli in solid phase (after centrifugation), this being despite the complexity of certain deposits. Furthermore, the bacterium could also be identified in liquid phase, in concentrations equal to those of a crude outlet, justifying the validity of the process as a tool for preparing a mass spectrometry sample.

An antibiotic susceptibility test is carried out by means of a VITEK2 automated device. Briefly, 3 ml of 0.45% saline suspension (bioMérieux) calibrated at 0.5 McFarland are prepared from the microorganisms treated, and placed in the automated device (VITEK N° 503 cards, bioMérieux).

For this test, only E. coli is studied. However, the examination is carried out on a strain sensitive (ATCC 25922) to one of the antibiotics tested in the apparatus. The minimum inhibitory concentrations (MICs) are calculated and analyzed according to the CAST (Europe) and CLSI (USA) databases. No difference in interpretation is to be reported on

*E. coli* ATCC 25922 between the solution extracted by acoustophoresis, the solution extracted by means of a conventional sample preparation protocol and a control (fresh culture).

Figure 22:
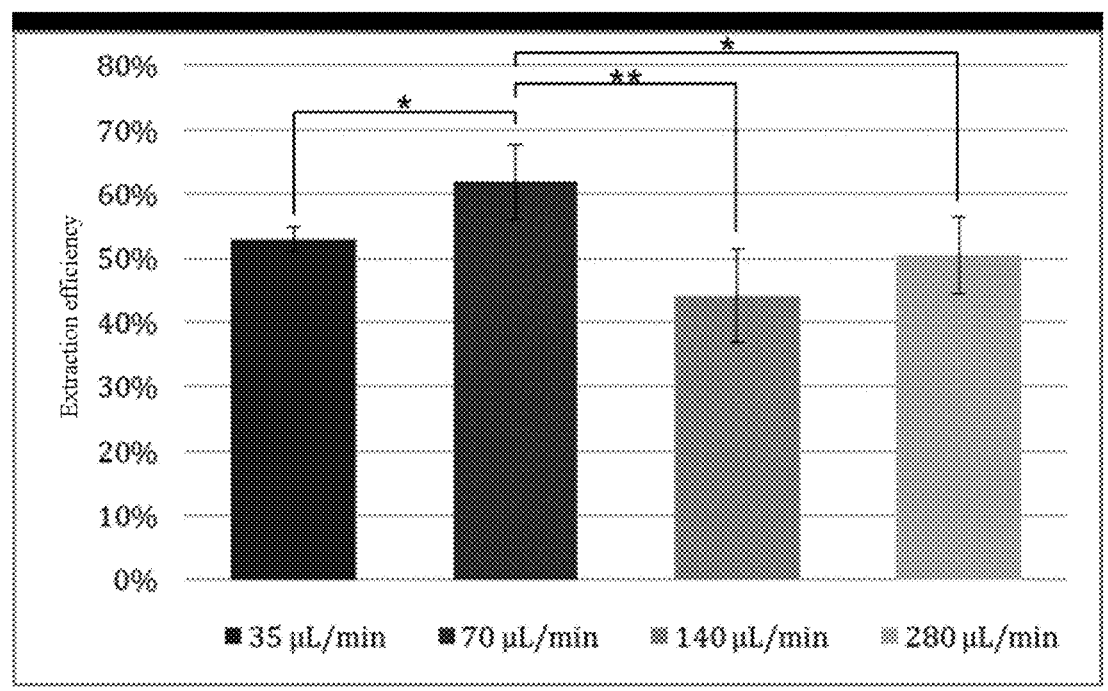
FIG. 22 is a diagram illustrating the impact of the flow rate of extractor buffer on the extraction efficiency.

Characterization of the Acoustophoresis on an Inoculated Blood Culture:

Optimum of Extraction (in Terms of Flow Rate) on *E. Coli*:

The optimal buffer flow rate for a blood culture inoculated with *E. coli* was determined in terms of extraction efficiency. The sample flow rate is fixed at 60 µl/min, and the frequency is adjusted manually so as to visually preserve the focusing of the red blood cells. The performance levels resulting from the various buffer flow rates are presented in FIG. 22 (extractions of three different blood cultures, all on the first day after color change of the pellet of the blood culture bottle). According to FIG. 22, a buffer flow rate of 70 µl/min allows a mean microorganism extraction efficiency of 62%, significantly higher than the other experimental points studied. This extraction efficiency on *E. Coli* blood culture is greatly superior to the prior art processes using the acoustophoresis technique, this being starting from a blood culture not diluted prior to introduction into an acoustophoresis device. According to these results, the experimental point [sample flow rate=60 µl/min; buffer flow rate=70 µl/min] is adopted as an optimum point of extraction on an *E. coli* inoculated blood culture.

Figure 23:
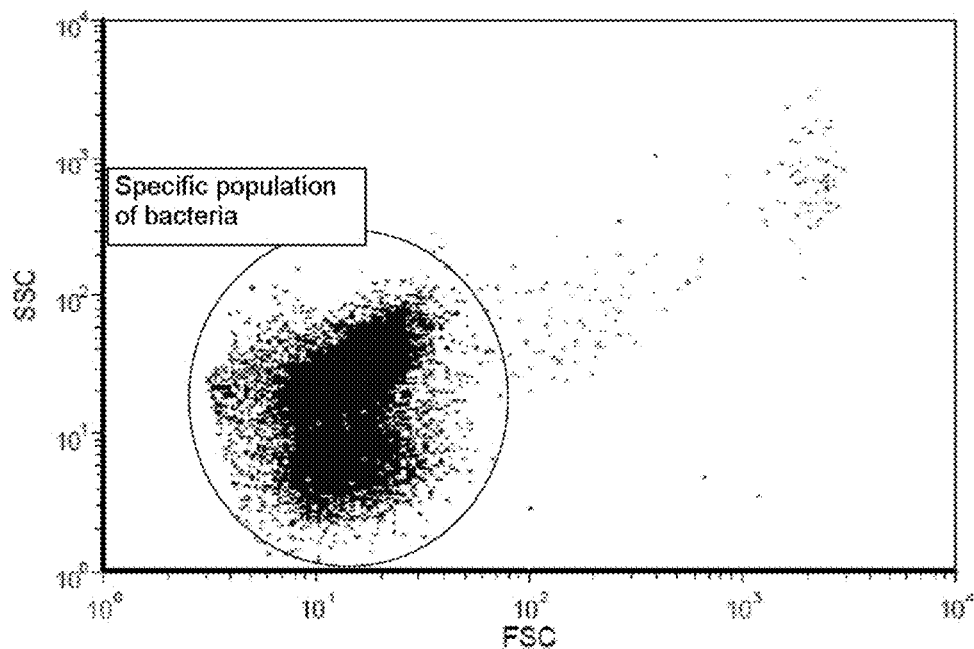
FIG. 23 illustrates the result of the flow cytometry analysis (scattergram) of a sample decomplexified by the treatment method according to the invention.

This regulation also allows great purity of the peripheral (side) channels. Indeed, as presented by way of indication in FIG. 23, more than 99% of the events detected correspond to bacteria (counting by flow cytometry). Very few leaks are observed in the side channels, which is confirmed by the low representation of the blood cells in the scattergram of FIG. 23. It should be noted that this experimental operation point limits the dilution during separation, allowing recovery of concentrated side outputs. The *E. Coli* concentration is thus estimated at between $6.25 \times 10^8$ and $7.75 \times 10^8$ CFU/ml.

Advantageously, the adjustment of the frequency can be resolved by using a system for automatic detection of the resonance of the channel allowing regulation of the control signal from the piezoelectric transducer according to the variations in temperature of the device.

In the same way, various flow cytometry counting tests are carried out while modifying the volume ratio of Percoll in the extraction buffer containing physiological saline at 10% v/v, 5% v/v and 1% v/v. It is observed that the efficiency decreases with the increase in the volume ratio of Percoll. The use of a buffer of physiological saline adjusted to 1% (v/v) of Percoll is thus favored.

Post-Extraction Return to Growth:

The return to growth for the three species studied is equivalent to or even faster than a return to growth following conventional isolation on a dish. For each bacterial solution, the microorganisms undergo a lag phase of approximately one hour, before entering into the exponential phase for up to 4-5 h of culture, at which time a plateau begins to be reached. For each yeast solution, the microorganisms undergo a lag phase much longer than for the bacteria, ranging from 3 to 4 hours, before entering the exponential phase.

This example shows the capacity of the process according to the invention to treat samples capable of containing microorganisms and originating from blood cultures and also from sterile fluids grown in a culture medium. Culture media capable of receiving sterile body fluids can in particular be blood culture bottles. It is also demonstrated that the process according to the invention makes it possible to carry out an identification and antibiogram step on the concentrated sample.

The treatment method according to the invention allows extraction of microorganisms without the use of selective lysis buffer and without dilution of the sample prior to its introduction into an acoustophoresis device, for identification and antibiogram, this being regardless of the identification or antibiogram method used.

The treatment method according to the invention allows the direct use of undiluted positive blood culture bottle or blood culture, by taking a sample of, for example, 1 ml or more from the positive bottle for extraction by means of the process of the invention.

It is also demonstrated that a flow rate of 60 µl/min makes it possible to treat approximately 1 ml in 20 mn.

Advantageously, a device as described in FIG. 6*b* makes it possible to increase the microorganism collection yield by carrying out two successive steps of separation by acoustophoresis.

Figure 24:
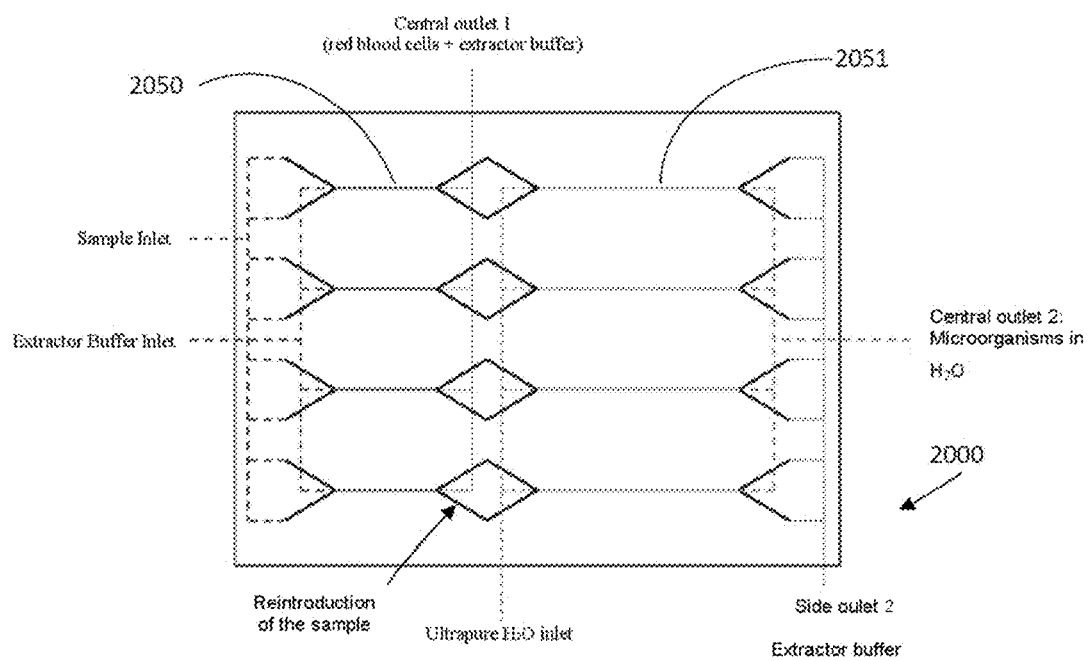
FIG. 24 illustrates a device according to the invention comprising four pairs of two successive separation channels and allowing the buffer used to be changed between the two separation steps.
Figure 25:
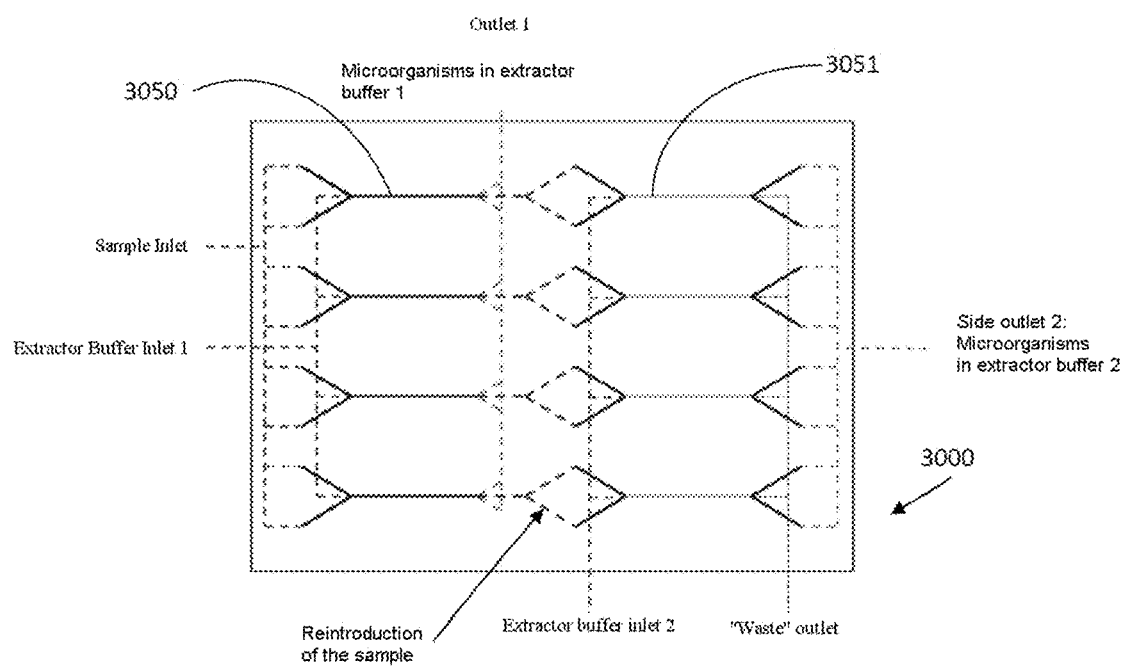
FIG. 25 illustrates a device according to the invention comprising two successive separation channels.

The invention also relates to a device and the use of a device comprising two successive separation channels, as illustrated in FIGS. 24 and 25. These devices can be produced in the same way as the devices previously described. Likewise, one or more transducers can be attached to the devices in order to carry out two steps of separation by acoustophoresis in the successive separation channels.

FIG. 24 illustrates a device 2000 according to the invention comprising two successive separation channels 2050, 2051 and allowing the buffer used to be changed between the two separation steps within these channels. The device 2000 comprises an inlet for the sample, and an inlet for the "extractor" buffer, namely the buffer used for the first step of separation by acoustophoresis. It also comprises a first "central outlet 1" outlet allowing recovery of the red blood cells extracted in the extraction buffer. The first separation step within the channel 2050 is thus the site of what is strictly speaking the microorganism extraction. The device also comprises a second inlet allowing the introduction of a second extraction buffer into the second separation channel 2051. This makes it possible in particular to carry out a second step allowing the extraction buffer used to be changed, for example for purified water. The side outputs of the channel 2050 are reintroduced into the side inlets of the channel 2051. Advantageously, the channel 2051 is longer than the channel 2050 in order to improve the yield of the second separation step. This second allows the transfer of the microorganisms from the buffer of the first separation step to the buffer of the second separation step. The central outlet 2 of the channel 2051 makes it possible to recover microorganisms in purified water. The side outlets make it possible to recover the extractor buffer, used in the first separator step, with a lower microorganism concentration than following the first separation step. The succession of the separation steps using two different buffers thus makes it possible to increase the concentration of sample prepared and to have microorganisms in a buffer that can be used directly for an identification step, for example by mass spectrometry.

Advantageously, a device as described in FIG. 6*c* makes it possible to retreat the microorganism recovery outputs (originating from the channels 1370*a* and 1370*c*) by concentrating the microorganisms in the separation channel 1350' in order to recapture and to increase the capture yield in an ad-hoc buffer (for example water) allowing an identification by MALDI-TOF or LC-ESI-MS/MS. For this, the ad-hoc buffer is introduced from the orifice 1330*b*'. Alternatively, the buffer introduced into the orifice 1330b' can be a buffer which allows rapid return to growth, ideal for performing an antibiogram.

FIG. 25 illustrates a device 3000 according to the invention comprising two successive separation channels 3050, 3051 and allowing the buffer used to be changed between the two separation steps. The central output of the separation channel 3050 is reintroduced into the side inlets of the channel 3051. The device 3000 comprises an inlet for the sample, and an inlet for the "extractor" buffer 1, namely the buffer used for the first step of separation by acoustophoresis. It also comprises a first outlet, "outlet 1", allowing the recovery of the microorganisms extracted in the extractor buffer 1. The first separation step within the channel 3050 is thus the site of what is strictly speaking a first extraction step, the microorganisms being focused toward the side outlets of the channel 3050. The device 3000 also comprises a second inlet allowing the introduction of a second extraction buffer (extraction buffer 2) into the second separation channel 3051. This makes it possible in particular to carry out a second extraction step improving the overall yield of the microorganism extraction. Advantageously, the channel 3051 is longer than the channel 3050 in order to improve the yield of the second separation step. The central outlet of the channel 3051 is then a waste outlet and the second side outlet (side outlet 2) makes it possible to recover microorganisms in extractor buffer 2.

The devices 2000 and 3000 advantageously have several pairs of successive separation channels as described and operating in parallel, the sample and buffer inlets and outlets being distributed in the pairs of channels by introduction, conveying and suctioning networks as previously described. The parallelization of the successive separations thus makes it possible to increase the volume of sample prepared and to have microorganisms in a buffer that can be used directly for an identification step, for example by mass spectrometry.

Also described is an example of implementation of the process according to the invention using the devices 500, 600, comprising the steps consisting in:
  Depositing 1 ml of positive blood culture in the inlet wells 530a and introducing the ad-hoc extraction buffer into the well 530b.
  Coupling the wells, for example using a lid 1110, in order to connect the inlet and outlet wells to syringe drivers or pressure reservoirs integrated into an associated instrument.
  Introducing the blood culture sample.
    Stabilizing the flow for a few minutes by activating the piezoelectric transducer, the red blood cells going to a first waste outlet connected to the central outlet channel.
  Once the focusing bundle has been stabilized, collecting the microorganisms toward the two peripheral outlets in one and the same tube.
  Optionally returning to circulation (in the same acoustophoresis device or in a new device) the microorganisms collected in order to concentrate them in an ad-hoc buffer (non-saline or suitable for rapid return to growth) in order to be able to carry out an identification by MALDI mass spectrometry or an antibiogram.
  Optionally returning to circulation (in the same acoustophoresis device or in a new device) the waste outlet in order to increase the microorganism collection yield.
  Identifying the microorganisms or performing an antibiogram.

REFERENCES

[1] Ai, Y., Sanders, C. K., & Marrone, B. L. (2013). Separation of *Escherichia coli* bacteria from peripheral blood mononuclear cells using standing surface acoustic waves. Analytical chemistry, 85(19), 9126-9134.

The invention claimed is:

1. A method for treating a sample from a blood culture or a sample of sterile body fluid which may contain one or more microorganism(s) of interest, the method comprising a decomplexification step that comprises the following steps:
  (i) enriching the sample by incubation,
  (ii) introducing all or part of the sample following the enrichment into a first inlet orifice of an acoustophoresis device without dilution prior to the introduction,
  (iii) introducing a buffer into a second inlet orifice of the acoustophoresis device, the inlet orifices being fluidically connected to at least two outlet orifices by at least one separation channel, the buffer and the sample being introduced at respective flow rates capable of generating a laminar flow in the separation channel,
  (iv) separation of separating the sample by acoustophoresis so as to promote the concentration of non-specific particles present in the sample in at least one of the outlet orifices of the acoustophoresis device,
  (v) obtaining an enriched and decomplexified sample, and
  (vi) identifying the microorganism(s) present in the enriched and decomplexified sample by means of a mass spectrometry method,
  wherein the acoustophoresis is carried out with a frequency between 300 kHz and 10 MHz.

2. The treatment method according to claim 1, further comprising a second decomplexification step that comprises separating the enriched and decomplexified sample by acoustophoresis so as to promote a greater recovery rate of the microorganism(s) still present in the enriched and decomplexified sample in at least one of the outlet orifices of the acoustophoresis device.

3. The treatment method according to claim 1, further comprising a second decomplexification step that comprises separating the enriched and decomplexified sample by acoustophoresis so as to promote a greater rejection rate of non-specific particles present in the enriched and decomplexified sample in at least one of the outlet orifices of the acoustophoresis device.

4. The treatment method according to claim 2, wherein the acoustophoresis device comprising at least two successive separation channels.

5. The treatment method according to claim 1, wherein the buffer used is of different nature and/or of different density relative to the sample.

6. The treatment method according to claim 1, further comprising
  measuring the optical density of the enriched and decomplexified sample during or following the separation by acoustophoresis so as to obtain a sample having a defined optical density.

7. The treatment method according to claim 1, further comprising incubating the enriched and decomplexified sample.

8. The treatment method according to claim 7, further comprising shaking the enriched and decomplexified sample during the incubation.

9. The treatment method according to claim 7, further comprising measuring the optical density of the enriched and decomplexified sample during or following the incubation, so as to stop or prolong the incubation to adjust the sample by dilution when a defined optical density threshold is measured.

10. The treatment method according to claim 1, further comprising analyzing susceptibility of the microorganism(s)

present in the sample to one or more antibiotic(s) by early imaging of the inhibitory zones obtained on culture medium using an antibiotic disk or an antibiotic strip, or by means of a biochemical test, wherein the antibiotic(s) are determined by the result of the identification of the microorganism(s).

11. The treatment method according to claim 1, wherein all or part of the enriched and decomplexified sample is transferred into the wells of a microplate or into various wells in fluidic connection with at least one of the outlet orifices containing all or part of the sample.

12. The treatment method according to claim 11, further comprising incubating the enriched and decomplexified sample directly in the microplate.

13. The treatment method according to claim 11, further comprising adjusting the optical density of the enriched and decomplexified sample directly in the microplate.

14. The treatment method according to claim 11, wherein each of the wells is, after an incubation time greater than or equal to 1 h in the presence of an antibiotic(s) which is different and/or an antibiotic in different concentrations, successively suctioned so as to be analyzed by flow cytometry.

15. The treatment method according to claim 14, further comprising detecting by flow cytometry analysis a shift in the fluorescence signal between microorganisms which are sensitive, intermediate or resistant to the antibiotics tested with the enriched and decomplexified sample.

16. The treatment method according to claim 1, further comprising carrying out mechanical or enzymatic lysis of the enriched and decomplexified sample, and then extracting nucleic acids and analyzing the nucleic acids by PCR, qPCR or sequencing.

17. The treatment method according to claim 1, further comprising capturing a species present in the enriched and decomplexified sample using magnetic particles followed by separation by magnetophoresis.

18. The treatment method according to claim 2, wherein the first decomplexification step is carried out using a first buffer, and the second decomplexification step is carried out with a second buffer, distinct from the first buffer.

19. The treatment method according to claim 18, wherein the first buffer is isotonic and comprises Percoll at a volume ratio of less than or equal to 10%.

20. The treatment method according to claim 1, further comprising determining an antibiogram profile of the microorganism(s) that has (have) been identified.

21. The treatment method according to claim 20, wherein an antibiogram test of the microorganism(s) is carried out by flow cytometry, by early imaging of the inhibitory zones obtained on culture medium using an antibiotic disk or an antibiotic strip, or by means of a biochemical test.

22. The treatment method according to claim 1, wherein the separation channel has a length that is between 35 mm and 80 mm, a lower width that is between 300 μm and 375 μm, an upper width that is between 550 μm and 625 μm, a depth that is between 100 μm and 150 μm, and a D-shaped cross-section.

23. An acoustophoresis device comprising:
at least two inlets;
at least one separation channel to which the inlets are fluidically connected by conveying channels;
at least two outlets to which the separation channel is fluidically connected by conveying channels; and
at least one integrated transducer having a frequency of between 300 kHz and 10 MHz that is inside or adjacent to a wall of the separation channel,
wherein the separation channel has a length that is between 35 mm and 80 mm, a lower width that is between 300 μm and 375 μm, an upper width that is between 550 μm and 625 μm, a depth that is between 100 μm and 150 μm, and a D-shaped cross-section.

* * * * *